(12) United States Patent
Meagher et al.

(10) Patent No.: US 7,667,096 B2
(45) Date of Patent: Feb. 23, 2010

(54) CONDITIONAL STERILITY IN PLANTS

(75) Inventors: Richard B. Meagher, Athens, GA (US); Elizabeth McKinney, Athens, GA (US); Tehryung Kim, Taejeon (KR)

(73) Assignee: University of Georgia Research Foundation, Inc., Athens, GA (US)

( * ) Notice: Subject to any disclaimer, the term of this patent is extended or adjusted under 35 U.S.C. 154(b) by 223 days.

(21) Appl. No.: 10/559,301

(22) PCT Filed: Jun. 3, 2004

(86) PCT No.: PCT/US2004/018058
§ 371 (c)(1), (2), (4) Date: Mar. 31, 2006

(87) PCT Pub. No.: WO2005/001101
PCT Pub. Date: Jan. 6, 2005

(65) Prior Publication Data
US 2007/0101459 A1    May 3, 2007

Related U.S. Application Data

(60) Provisional application No. 60/475,551, filed on Jun. 3, 2003.

(51) Int. Cl.
*C12N 15/82* (2006.01)
*C12N 15/54* (2006.01)
*A01H 1/02* (2006.01)
*A01H 5/00* (2006.01)

(52) U.S. Cl. .................. 800/286; 800/271; 800/274; 800/287; 800/303; 800/306; 800/317; 800/319; 800/320; 800/285; 435/194

(58) Field of Classification Search .......... None
See application file for complete search history.

(56) References Cited

U.S. PATENT DOCUMENTS

| | | | |
|---|---|---|---|
| 5,110,732 A | 5/1992 | Benfey et al. |
| 5,401,836 A | 3/1995 | Baszczynski et al. |
| 5,459,252 A | 10/1995 | Conkling et al. |
| 5,510,471 A | 4/1996 | Labrun et al. |
| 5,545,545 A | 8/1996 | Gengenbach et al. |
| 5,633,363 A | 5/1997 | Colbert et al. |
| 5,635,618 A | 6/1997 | Capellades et al. |
| 5,641,876 A | 6/1997 | McElroy et al. |
| 5,668,294 A | 9/1997 | Meagher et al. |
| 5,808,034 A | 9/1998 | Bridges et al. |
| 5,837,876 A | 11/1998 | Conkling et al. |
| 5,962,769 A | 10/1999 | Albertsen et al. |
| 5,965,796 A | 10/1999 | Meagher et al. |
| 6,005,167 A | 12/1999 | Van Tunen et al. |
| 6,172,279 B1 | 1/2001 | Bridges et al. |
| 6,372,967 B1 | 4/2002 | Mariani et al. |
| 6,384,304 B1 | 5/2002 | Quandt et al. |
| 6,506,550 B1 | 1/2003 | Fulton et al. |
| 6,512,164 B1 | 1/2003 | Famodu et al. |
| 6,518,483 B1 | 2/2003 | Bruce et al. |
| 6,518,485 B1 * | 2/2003 | Connett-Porceddu et al. ............ 800/293 |
| 2002/0157129 A1 | 10/2002 | Perez et al. |
| 2003/0135885 A1 | 7/2003 | Lanahan et al. |
| 2003/0135888 A1 | 7/2003 | Zhu et al. |
| 2004/0013658 A1 | 1/2004 | Fulton et al. |
| 2005/0198707 A1 | 9/2005 | Meagher et al. |

FOREIGN PATENT DOCUMENTS

| | | |
|---|---|---|
| EP | 0628635 | 12/1994 |
| WO | 9325695 | 12/1993 |
| WO | WO 98/13503 | * 4/1998 |
| WO | 9827201 | 6/1998 |
| WO | 9839462 | 9/1998 |
| WO | 9904023 | 1/1999 |
| WO | 0000623 | 1/2000 |
| WO | 0129237 | 4/2001 |
| WO | 0248335 | 6/2002 |
| WO | 03066823 | 8/2003 |

OTHER PUBLICATIONS

Kandasamy et al. (Mar. 2003) "Cell Cycle-Dependent Association of *Arabidopsis* Actin-Related Proteins AtARP4 and AtARP7 with the Nucleus," Plant J. 33:393-348.

(Continued)

*Primary Examiner*—David T Fox
(74) *Attorney, Agent, or Firm*—Greenlee, Winner and Sullivan, P.C.

(57) ABSTRACT

The present disclosure provides methods, recombinant DNA molecules, recombinant host cells containing the DNA molecules, and transgenic plant cells, plant tissue and plants which contain and express at least one antisense or interference RNA specific for a thiamine biosynthetic coding sequence or a thiamine binding protein or a thiamine-degrading protein, wherein the RNA or thiamine binding protein is expressed under the regulatory control of a transcription regulatory sequence which directs expression in male and/or female reproductive tissue. These transgenic plants are conditionally sterile; i.e., they are fertile only in the presence of exogenous thiamine. Such plants are especially appropriate for use in the seed industry or in the environment, for example, for use in revegetation of contaminated soils or phytoremediation, especially when those transgenic plants also contain and express one or more chimeric genes which confer resistance to contaminants.

12 Claims, 14 Drawing Sheets

OTHER PUBLICATIONS

Kandasamy et al. (Jan. 2002) "Functional Non-Equivalency of Actin Isovariants in *Arabidopsis*," Mol. Biol. Cell 13:251-261.

Kandasamy et al. (1999) "The Late Pollen-Specific Actins in Angiosperms," Plant. J. 18:681-691.

Kellermann et al. (1990) "Pyruvate decarboxylase Isozyme 1," NCBI Accession No. PO6169.

Kim et al. (1998) "A Brassica cDNA Clone Encoding a Bifunctional Hydroxymethylpyrimidine Kinase/Thiamin-Phosphate Pyrophosphorylase Involved in thiamin Biosynthesis," Plant Mol. Biol. 37(6):955-965.

Kursteiner et al. (Jun. 2003) "The Pyruvate decarboxylase1 Gene of *Arabidopsis* Is Required During Anoxia but not Other Environmental Stresses," Plant Physiol. 132:968-978.

Lauter, F.R. (1996) "Root Specific Expression of the LeRse-1 Gene in Tomato is Induced by Exposure of the Shoot to Light," Mol. Gen. Genet. 252:751-754.

Ledoux et al. (May 1974) "DNA-Mediated Genetic Correction of Thiamineless *Arabidopsis thaliana*," Nature 249:17-21.

Li et al. (1969) "Thiamine Mutants of the crucifer, *Arabidopsis*," Biochem. Genet. 3:163-170.

Machado et al. (1996) "Thi1, a Thiamine Biosynthetic Gene in *Arabidopsis thaliana*, Complements Bacterial Defects in DNA Repair," Plant. Mol. Biol. 31:585-593.

Machado et al. (1997) "Dual Role for the Yeast THI4 Gene in Thiamine Biosynthesis and DNA Damage Tolerance," J. Mol. Biol. 273:114-121.

Manetti et al. (1994) "nmt2 of Fission Yeast: A Second Thiamine-Repressible Gene Co-Ordinately Regulated with nmt1," Yeast 10:1075-1082.

Mariani et al. (Jun. 1992) "A Chimaeric Ribonuclease-Inhibitor Gene Restores Fertility to Male Sterile Plants," Nature 357:384-387.

McDowell et al. (Feb. 1996) "Structure and Evolution of the Actin Gene Family in *Arabidopsis thaliana*," Genetics 142:587-602.

McDowell et al. (1996) "The *Arabidopsis* ACT7 Actin Gene is Expressed in Rapidly Developing Tissues and Responds to Several External Stimuli." Plant Physiol. 111:699-711.

McKinney et al. (May 2001) "Small Changes in the Regulation of one *Arabidopsis* Profilin Isovariant, prf1, Alter Seedling Development," Plant Cell 13:1179-1191.

McKinney et al. (Mar. 2002) "*Arabidopsis* Contains Ancient Classes of Differentially Expressed Actin- Related Protein Genes," Plant. Physiol. 128:997-1007.

Meagher, R.B. (2000) "Phytoremediation of Toxic Elemental and Organic Pollutants," Curr. Opin. Plant. Biol. 3:153-162.

Meagher et al. (2003) "The *Arabidopsis* Cytoskeletal Genome," In: The *Arabidopsis* Book, American Society of Plant Biologists, 26 pages.

Meagher et al. (1996) "Phytoremediation of Heavy Metal Pollution: Ionic and Methyl Mercury," In; OECD Biotechnology for Water use and Conservation Workshop (Cocoyoc, Mexico: Organization for Economic Co-Operation and Development), pp. 305-321.

Moffatt et al. (1988) "Positive Selection for Male-Sterile Mutants of *Arabidopsis* Lacking Adenine Phosphoribosyl Transferase Activity," Plant Physiol. 86:1150-1154.

Murray et al. (1989) "Codon Usage in Plant Genes," Nucle. Acids Res. 17:477-498.

Nishimura (Apr. 1991) "A Constitutive Thiamine Metabolism Mutation, thi80, Causing Reduced Thiamine Pyrophosphokinase Activity in *Saccharomyces cerevisiae*," J. Bacteriol. 173:2716-2719.

Nishimura et al. (Jul. 1992) "A Positive Regulatory Gene, THI3, is Required for Thiamine Metabolism in *Saccharomyces cerevisiae*," J. Bacteriol. 174:4701-4706.

Nishimura et al. (1993) "THI3 Regulatory Protein, (*Saccharomyces cerevisiae*)," NCBI Accession No. BAA04886.

Nitz et al. (2001) "Pyk10, A Seedling and Root Specific Gene and Promoter from *Arabidopsis thaliana*," Plant Sci. 161:337-346.

Nosaka et al. (Aug. 1993) "Isolation and Characterization of a Thiamin Pyrophosphokinase Gene, THI80, from *Saccharomyces cerevisiae*," J. Biol. Chem. 268:17440-17447.

Nosaka et al. (1993) "Thiamine pyrophosphokinase (TPK), (Thiamine kinase)," NCBI Accession No. P35202.

Perez-Prat et al. (May 2002) "Hybrid Seed Production and the Challenge of Propagating Male-Sterile Plants," Trends Plant. Sci. 7:199-203.

Pfahl (Jan. 1979) "Tight-Binding Repressors of the lac Operon: Selection System and in Vitro Analysis," J. Bacteriol. 137:137-145.

Preuss et al. (Jun. 1994) "Tetrad Analysis Made Possible in *Arabidopsis* by a Mutation of the QUARTET (QRT) Genes," Science 264:1458-1460.

Rapala-Kozik et al. (1999) "Ligand-Protein Interaction in Plant Seed Thiamine-Binding Proteins. Binding of Various Thiamine Analogues to the Sepharose-Immobilized Buckwheat-Seed Protein," J. Protein Chem. 18:721-728.

Redei et al. (Feb. 1969) "Effects of X-Rays and Ethyl Methanesulfonate on the Chlorophyll B Locus in the Soma and on the Thiamine Loci in the Germline of *Arabidopdis*," Genetics 61:453-459.

Robb et al. (2001) "Thiamine Phosphate Pyrophosphorylase" NCBI Accession No. NP_579063.

Rugh et al. (Jul. 1998) "Toxic Mercury Reduction and Remediation Using Transgenic Plants with a Modified Bacterial Gene," Hort. Sci. 33:12-15.

Rugh et al. (Oct. 1998) "Development of Transgenic Yellow Poplar for Mercury Phytoremediation," Nat. Biotechnol. 16:925-928.

Rugh et al. (Apr. 1996) "Mercury Ion Reduction and Resistance in Transgenic *Arabidopsis thaliana* Plants Expressing a Modified Bacterial merA Gene," Proc. Natl. Acad. Sci. USA 93:3182-3187.

Sabatini et al. (Feb. 2003) "SCARECROW is Involved in Positioning the Stem Cell Niche in the *Arabidopsis* Root Meristem," Genes Dev. 17:354-358.

Sequence NP_563669 "Thiamin diphosphokinase,".

Sequence NP_200288 "Thiazole Biosynthetic Enzyme, Chloroplast".

Sequence NP_195752 "Pyruvate Decarboxylase,".

Sequence NP_189045 "Hydroxyethylthiazole Kinase Family Protein".

Sequence NP_173707 "Thiamin Biosynthesis Protein, Putative".

Sequence NP_172707 "Unknown Protein".

Shirley et al. (1987) "5' Proximal Sequences of a Soybean Ribulose-1,5-Bisphosphate Carboxylase Small Subunit Gene Direct Light and Phytochrome Controlled Transcription," Nuc. Acids Res. 15:6501-6514.

Shoemaker et al. (1999) "Glycine max cDNA Clone," NCBI Accession No. BM177583.

Shoemaker et al. (1999) "Glycine max cDNA Clone," NCBI Accession No. BG725189.

Shoemaker et al. (1999) "Glycine soja cDNA Clone," NCBI Accession No. BM524834.

Shoemaker et al. (1999) "Glycine max cDNA Clone," NCBI Accession No. BU964708.

Sotolongo et al. (1999) "Saccharum Officinarum Partial mRNA for Pyruvate Decarboxylase," NCBI Accession No. AJ251246.

Aharoni et al. (2000) "Fragaria X Ananassa Pyruvate Decarboxylase," NCBI Accession No. AF193791.

An et al. (1996) "Strong, Constitutive Expression of the *Arabidopsis* ACT2/ACT8 Actin Subclass in Vegetative Tissues," Plant J. 10:107-121.

*Arabidopsis* Genome Initiative (2000) "Analysis of the Genome Sequence of the Flowering Plant *Arabidopsis thaliana*," Nature 408:796-815.

Barabas et al. (1991) "Hybrid Seed Production Using Nutritional Mutants," *Euphytica* 53:67-72.

Bariola et al. (1999) "Regulation of S-Like Ribonuclease Levels in *Arabidopsis*. Antisense Inhibition of RNS1 of RNS2 Elevates Anthocyanin Accumulation," Plant Physiol. 119:331-342.

Bennett et al. (2002) "IRRI Drought Stress Panicle Library Oryza sativa (Indica Cultivar-Group) cDNA Clone C0003049 5' Similar to Probable Thiamine Biosynthetic Bifunctional Enzyme," NCBI Acession No. CA765813.

Betz et al. (1986) "Base Substitution Mutants of the lac Operator: In Vivo and In Vitro Affinities for lac Repressor," Gene 50:123-132.

Bizily et al. (Feb. 2003) "Subcellular Targeting of Methylmercury Lyase Enhances Its Specific Activity for Organic Mercury Detoxification in Plants," Plant Physiol. 131:463-471.

Bizily, S. (2001) "Genetic Engineering of Plants with the Bacterial Genes merA and merB for the Phytoremediation of Methylmercury Contaminated Sediments," In, Genetics Department (Athens GA, University of GA), pp. 145.

Bizily et al. (2000) "Phytodetoxification of Hazardous Organomercurials by Genetically Engineered Plants," Nat. Biotechnol. 18:213-217.

Bizily et al. (1999) "Phytoremediation of Methylmercury Pollution: merB Expression in *Arabidopsis thaliana* Confers Resistance to Organomercurials," Proc. Natl. Acad. Sci. USA 96:6808-6813.

Blattner et al. (1997) "Hydroxyethylthiazole Kinase, (*Escherichia coli* K12)," NCBI Accession No. NP_416607.

Bouvier et al. (1998) "Dedicated Roles of Plastid Transketolases During the Early Onset of Isoprenoid Biogenesis in Pepper Fruits 1," Plant Physiol. 117:1423-1431.

Brown, S. (2001) "Cloning Vector pSB3616 Alkakine Phosphatase (phoA), lac Repressor (lacI), and Chloramphenicol Acetyltransferase (cat) Genes, Complete cds," NCBI Accession No. AY042185.

Brown et al. (1987) "Biosynthesis of Folic Acid, Roboflavin, Thiamine, and Pantothenic Acid," In; *Escherichia coli* and Salmonella Typhimurium, Neidhardt, F. ed., Washington, DC: American Society for Microbiology, pp. 521-538.

Bucher et al. (1995) "N. tabacum mRNA for Pyruvate Decarboxylase 2," NCBI Accession No. X81855.

Bui et al. (2002) "Scarlet Runner Bean Embryo-Proper Region Phaseolus coccineous cDNA 5' Similar to Pyruvate Decarboxylase Isozyme2, mRNA Sequence," NCBI Accession No. CA896675.

Bui et al. (2002) "Scarlet Runner Bean Embryo-Proper Region Phaseolus coccineous cDNA 5' Similar to Pyruvate Decarboxylase Isozyme 2, mRNA Sequence," NCBI Accession No. CA896676.

Bui et al. (2002) "Scarlet Runner Bean Suspensor Region TriplEx2 Phaseolus coccineus cDNA 0 Similar to Pyruvate Decarboxylase Isozyme 2, mRNA Sequence," NCBI Accession No. CA900838.

Bui et al. (2002) "Scarlet Runner Bean Suspensor Region TriplEx2 Phaseolus coccineus cDNA 5' Similar to Pyruvate Decarboxylase Isozyme 2, mRNA Sequence," NCBI Accession No. CA900839.

Bussey et al. (1997) "Bifunctional Enzyme with Thiamine-phosphate Pyrophosphorylase and 4-methyl-5-beta-hydroxyethythiazole Kinase Activities, Required for Thiamine Biosynthesis; GFP-Fusion Protein Localizes to the Cytoplasm in a Punctate Pattern, (*Saccharomyces cerevisiae*),"Sequence NP_015110.

Bussey et al. (1997) "Protein with Similarity to Hydroxymethylpyrimidine Phosphate Kinases" NCBI Accession No. NP_015446.

Chabregas et al. (2001) "Dual Targeting Properties of the N-Terminal Signal Sequence of *Arabidopsis thaliana* THI1 Protein to Mitochondria and Chloroplasts," Plant Mol. Biol. 46:639-650.

Chang et al. (1997) "Expression, Purification and Characterization of *Arabidopsis thaliana* Acetohydroxyacid Synthase," Biochem. J. 327:161-169.

Chang et al. (1999) "Aspartate-27 and Glutamate-473 are Involved in Catalysis by Zymomonas mobilis Pyruvate Decarboxylase," Biochem. J. 339:255-260.

Chuang et al. (Apr. 2000) "Specific and Heritable Genetic Interference by Double-Stranded RNA in *Arabidopsis thaliana*," Proc. Natl. Acad. Sci. USA 97:4985-4990.

Citovsky et al. (2000) "Systemic Transport of RNA in Plants," Trends Plant Sci. 5:52-54.

Conkling et al. (1990) "Isolation of Transcriptionally Regulated Root-Specific Genes from Tobacco," Plant Physiol. 93:1203-1211.

Costello et al. (1994) "*Bacillus thiaminolyticus* Thiaminase I Precursor Gene, Complete cds," NCBI Acession No. U17168.

Dhankher et al. (Nov. 2002) "Engineering Tolerance and Hyperaccumulation of Arsenic in Plants by Combining Arsenate Reductase and Gamma-Glutamylcysteine Synthetase Expression," Nat. Biotechnol. 20:1140-1145.

Fagard et al. (2000) "Systemic Silencing Signal(s),"Plant. Mol. Biol. 43:285-293.

Falcon et al. (2000) "Operator DNA Sequence Variation Enhances High Affinity Binding by Hinge Helix Mutants of Lactose Repressor Protein," Biochem. 39:11074-11083.

Fuerst et al. (Apr. 1989) "Transfer of the Inducible lac Repressor/Operator System from *Escherichia coli* to a Vaccinia Virus Expression Vector," Proc. Natl. Acad. Sci USA 86:2549-2553.

Gao et al. (Dec. 2000) "Fungal Pathogen Protection in Potato by Expression of a Plant Defensin Peptide," Nat. Biotechnol. 18:1307-1310.

Goddemeier et al. (1998) "Root Specific Expression of a Zea mays Gene Encoding a Novel Glycine-Rich Protein, zmGRP3," Plant Mol. Biol. 36:799-802.

Goffeau et al. (1996) "Thi2p, (*Saccharomyces cerevisiae*)," NCBI Accession No. NP_009799.

Goffeau et al. (Oct. 1996) "Life with 6000 Genes," Science 274:546-567.

Goldfarb et al. (1986) "Synthetic Peptides as Nuclear Localization Signals," Nature 322:641-644.

Hamilton et al. (Oct. 1999) "A Species of Small Antisense RNA in Posttranscriptional Gene Silencing in Plants," Science 286:950-952.

Hayashi et al. (2001) "Thiamine-phosphate pyrophosphoiylase, (*Escherichia coli* 0157:H7)," NCBI Accession No. NP_312943.

Heaton et al. (1998) "Phytoremediation of Mercury and Methylmercury Polluted Soils Using Genetically Engineered Plants," J. Soil Contam. 7:497-509.

Held et al. (1993) "An mRNA Putatively Coding for an O-Methyltransferase Accumulates Preferentially in Maize Roots and is Located Predominantly in the Region of the Endodermis," Plant Physiol. 102:1001-1008.

Held et al. (1997) "Zrp2: A Novel Maize Gene Whose mRNA Accumulates in the Root Cortex and Mature Stems," Plant. Mol. Biol. 35:367-375.

Hu et al. (1990) "A Combination of Depression of the lac Operator-Repressor System with Positive Induction by Glucocorticoid and Metal ions Provides a High-Level-Inducible Gene Expression System Based on the Human Metallothionein-IIA Promoter," Mol. Cell. Biol. 10:6141-6151.

Huang et al. (1996) "The *Arabidopsis thaliana* ACT4/ACT12 Actin Gene Subclass is Strongly Expressed in Post-Mitotic Pollen," Plant. J. 10:189-202.

Huang et al. (1997) "The *Arabidopsis* ACT11 Actin Gene is Strongly Expressed in Tissues of the Emerging Inflorescence, Pollen and Developing Ovules," Plant. Mol. Biol. 33:125-139.

Huq et al. (1995) "Oryza sativa Pyruvate Decarboxylase 2 (Pdc2) mRNA, Complete cds," NCBI Accession No. U27350.

Huq et al. (1995) "Oryza sativa Pyruvate Decarboxylase 2 (Pdc2) mRNA, Complete cds," NCBI Accession No. U38199.

Iqbal et al. (Dec. 2002) "A Pyramid of Loci for Partial Resistance to *Fusarium solani* f. sp. Glycines Maintains Myo-Inositol-1-Phosphate Synthase Expression in Soybean Roots," Theor. Appl. Genet. 105:1115-1123.

Jefferson et al. (1987) "GUS Fusions: β-Glucuronidase as a Sensitive and Versatile Gene Fusion Marker in Higher Plants," EMBO J. 6:3901-3907.

Tanaka et al. (1990) "Enhancement of Foreign Gene Expression by a Dicot Intron in Rice But Not in Tobacco is Correlated with an Increased Level of mRNA and an Efficient Splicing of the Intron," Nuc. Acids Res. 18:6767-6770.

Tettelin et al. (1997) "Protein Required for Thiamine Biosynthesis and for Mitochondrial Genome Stability, (*Saccharomyces cerevisiae*)," NCBI Accession No. NP_011660.

Tsuchiya et al. (1995) "Tapetum-Specific Expression of the Gene for an Endo-β-1,3-Glucanase Causes Male Sterility in Transgenic Tobacco," Plant Cell Physiol. 36(3):487-494.

Ulmasov et al. (1997) "Regulated Expression of Plant tRNA Genes by the Prokaryotic tet and lac Repressors," Plant Mol. Biol. 35:417-424.

Voinnet et al. (Sep. 2000) "A Viral Movement Protein Prevents Spread of the Gene Silencing Signal in *Nicotiana benthamiana*," Cell 103:157-167.

Voinnet et al. (Nov. 1999) "Suppression of Gene Silencing: A General Strategy Used by Diverse DNA and RNA Viruses of Plants," Proc. Natl. Acad. Sci. USA 96:14147-14152.

Wang et al. (2002) "Salt Stressed Zea mays Root cDNA Library Zea mays cDNA Clone RNOSEQ1E11_T3.ab1 Similar to Pyruvate Decarboxylase," NCBI Accession No. BQ618938.

Watanabe et al. (1998) "Thiamine-Binding Protein from Sunflower Seeds," J. Nutr. Sci. Vintaminol. (Tokyo) 44:665-672.

Watanabe et al. (1998) "Characterization of Thiamin-Binding Protein from Buckwheat Seeds," J. Nutr. Sci. Vitaminol. 44:323-328.

Wood et al. (2002) "Hypothetical Protein SPBC26H8.01, (*Schizosaccharomyces pombe* 972h-)," NCBI Accession No. NP_596642.

Xu et al. (Mar. 1995) "Bcp1, A Gene Required for Male Fertility in *Arabidopsis*," Proc. Natl. Acad. Sci. USA 92:2106-2110.

Yamamoto et al. (1990) "Root-Specific Genes from Tobacco and *Arabidopsis* Homologous to an Evolutionary Conserved Gene Family of Membrane Channel Proteins," Nuc. Acids Res. 18:7449.

Yamamoto et al. (Apr. 1991) "Characterization of Cis-Acting Sequences Regulating Root-Specific Gene Expression in Tobacco," Plant Cell. 3:371-382.

\* cited by examiner

FIG. 4A

5' UTR - coding region -3' UTR

5'
1 accaaaccaaaccactcggtaaacttgtatagcctcttgtatatattatgatatatatca 60

61 ataataattacacgtgtaatgtaagatgcattttgatttgaagatgcattatgctgattt 120

121 gtaaaacataaacggctttggtccctttttagtgtgtccgaatgaataaggtgttcaaaa 180

181 tagcgtgtgatttgtaatttgtaatttgtaattagtctgaaacgttgtatatatgaatat 240

241 tcttcaattatataaaagcttgctttcaaatatatcaatttatctatcttttgattatat 300

301 tgtcccttttcgtggaccacaagtattaacttatctcatacaaataattcgtgcttaag 360

361 tttggtgttaaaattattgaaaattgatttacattgaattttttttcgcggtaattgataa 420

421 ttcatgaaaatcgatgaaatttactaatttatttcacattaaagtcaataaaatgggaa 480

481 aatatttgatgagaataaaataaaataaaataaagagaagggacgagaa<u>ATGAATAGCTT</u> 540

Boxed targeting sequence removed for bacterial expression and to eliminate a
unwanted restriction site                           Gly codon added to create NcoI site
541 <u>AGGAGGAATTAGGAGTTGGCCGGCGAATTGGAGAAGTACGACGGCGTCA<u>ATG</u>GGA</u>ACGAC 600
                                                     M   G   T   T  -
         A→T To remove unwanted KpnI site
601 GACGGAGAGCGTTAGAAAGGTTCCGCAAGTTTTAACAGTGGCGGGATCAGATTCCGGCGC 660
     T   E   S   V   R   K   V   P   Q   V   L   T   V   A   G   S   D   S   G   A  -

661 CGGAGCTGGAATTCAAGCCGACCTTAAAGTCTGCGCAGCTCGTGGTGTGTATTGCGCTTC 720
     G   A   G   I   Q   A   D   L   K   V   C   A   A   R   G   V   Y   C   A   S  -

721 CGTCATAACCGCAGTCACTGCTCAGAACACTCGAGGAGTTCAATCTGTTCATCTTCTTCC 780
     V   I   T   A   V   T   A   Q   N   T   R   G   V   Q   S   V   H   L   L   P  -

781 TCCGGAATTTATCTCTGAACAGCTCAAATCCGTCCTCTCTGACTTCGAATTCGACGTCGT 840
     P   E   F   I   S   E   Q   L   K   S   V   L   S   D   F   E   F   D   V   V  -

841 GAAGACTGGGATGCTTCCTTCTACTGAGATCGTTGAGGTTCTTCTTCAAAATCTATCAGA 900
     K   T   G   M   L   P   S   T   E   I   V   E   V   L   L   Q   N   L   S   D  -

901 TTTTCCAGTTCGTGGTAGAGATTACCTCGCTTTGTTCTCTTTGGTTGTTGATCCTGTGAT 960
     F   P   V   R   G   R   D   Y   L   A   L   F   S   L   V   V   D   P   V   M  -

961 GGTATCTACTAGTGGTCACGTTTTGGCTGGTTCTTCTATTCTCTCTATCTTTAGAGAGAG 1020

FIG. 4B

```
         V  S  T  S  G  H  V  L  A  G  S  S  I  L  S  I  F  R  E  R  -
1021 ATTACTACCAATTGCTGACATAATTACCCCAAATGTGAAAGAGGCTTCTGCTTTACTTGA 1080
         L  L  P  I  A  D  I  I  T  P  N  V  K  E  A  S  A  L  L  D  -
1081 TGGTTTTCGGATTGAGACTGTTGCAGAAATGCGGTCTGCAGCAAAGTCGTTGCATGAAAT 1140
         G  F  R  I  E  T  V  A  E  M  R  S  A  A  K  S  L  H  E  M  -
1141 GGGTCCTAGATTCGTACTTGTTAAAGGTGGTGATCTTCCTGACTCATCAGATTCAGTAGA 1200
         G  P  R  F  V  L  V  K  G  G  D  L  P  D  S  S  D  S  V  D  -
1201 TGTTTACTTTGATGGCAAGGAGTTTCATGAACTCCGTTCTCCTCGCATAGCTACAAGAAA 1260
         V  Y  F  D  G  K  E  F  H  E  L  R  S  P  R  I  A  T  R  N  -
1261 TACTCATGGGACTGGTTGCACTTTGGCTTCCTGTATTGCAGCTGAGCTTGCAAAAGGCTC 1320
         T  H  G  T  G  C  T  L  A  S  C  I  A  A  E  L  A  K  G  S  -
1321 TTCCATGCTCTCAGCCGTCAAGGTGGCTAAACGCTTTGTCGATAATGCCCTAGATTACAG 1380
         S  M  L  S  A  V  K  V  A  K  R  F  V  D  N  A  L  D  Y  S  -
1381 CAAAGATATTGTCATTGGCAGTGGGATGCAAGGACCTTTTGACCATTTTTTTGGTCTTAA 1440
         K  D  I  V  I  G  S  G  M  Q  G  P  F  D  H  F  F  G  L  K  -
1441 GAAGGATCCTCAAAGTTCTCGATGCAGCATATTCAATCCAGATGACCTGTTTCTATATGC 1500
         K  D  P  Q  S  S  R  C  S  I  F  N  P  D  D  L  F  L  Y  A  -
1501 TGTTACAGATTCTAGAATGAACAAAAAATGGAACCGTTCCATTGTGGATGCCTTGAAAGC 1560
         V  T  D  S  R  M  N  K  K  W  N  R  S  I  V  D  A  L  K  A  -
1561 TGCTATAGAGGGAGGGGCCACCATCATACAACTGAGGTTTGATCATTTTCTTGAAGAAGC 1620
         A  I  E  G  G  A  T  I  I  Q  L  R  F  D  H  F  L  E  E  A  -
1621 AAAAGCATGCATTGATATATGCCGGTCCCATGGAGTTAGTTTGCTGATAAACGACAGGAT 1680
         K  A  C  I  D  I  C  R  S  H  G  V  S  L  L  I  N  D  R  I  -
1681 CGACATTGCCCTTGCTTGTGATGCTGATGGAGTCCATGTTGGTCAATCCGACATGCCGGT 1740
         D  I  A  L  A  C  D  A  D  G  V  H  V  G  Q  S  D  M  P  V  -
1741 TGATCTAGTTCGGTCTCTTCTTGGCCCGGACAAGATCATAGGGGTCTCATGTAAGACACC 1800
         D  L  V  R  S  L  L  G  P  D  K  I  I  G  V  S  C  K  T  P  -
1801 AGAACAAGCTCATCAAGCATGGAAAGATGGTGCGGACTACATTGGGTCAGGAGGAGTTTT 1860
         E  Q  A  H  Q  A  W  K  D  G  A  D  Y  I  G  S  G  G  V  F  -
1861 TCCAACGAACACTAAGGCCAACAATCGTACCATAGGACTTGATGGGCTAAAAGAAGTATG 1920
         P  T  N  T  K  A  N  N  R  T  I  G  L  D  G  L  K  E  V  C  -
1921 TGAAGCATCAAAATTACCGGTTGTTGCAATCGGAGGCATAGGGATCTCAAATGCTGGGTC 1980
         E  A  S  K  L  P  V  V  A  I  G  G  I  G  I  S  N  A  G  S  -
1981 TGTTATGCAGATCGATGCACCGAACCTAAAAGGTGTAGCAGTTGTGTCAGCTTTGTTCGA 2040
         V  M  Q  I  D  A  P  N  L  K  G  V  A  V  V  S  A  L  F  D  -
2041 CCAAGATTGTGTTTTGACTCAAGCTAAGAAGTTGCATAAAACGCTTAAAGAGAGCAAAAG 2100
         Q  D  C  V  L  T  Q  A  K  K  L  H  K  T  L  K  E  S  K  R  -
                 Boxed region used in Thi2-RNAi construct
```

FIG. 4C

```
2101 GGGAATTTGAaccaaaaggtgttttagttttgttttaggtgcttacaaaatgttgtaaa 2160
     G   I  *

2161 ccttttacttctttacttgatgtattttttttttttttgagaaagccagaaaagataa 2220

Lower case letters part of 3´UTR, upper case is CDS
2221 atagtaatgattgctacaaacattttacttccaaaaacttccaacattctcaaattctc 2280

2281 caagagataacatttgtgtatttcatttgccttcactcctctaagaaatttattgttaca 2340

2341 ggcagcaatctgaaaaatggaacaaaatttacctttgacaaaggtatctaatgcttgctt 2400

2401 acaaacaaacgatttaacttgcctctctatatacacatagccactggaatggtacaaaga 2460

2461 agatgaggtatttgacatattcttgttttgt                              2492
```

- Capital letters are coding region
- Small letters are UTRs
- Boxed area with thin line is deleted region
- Boxed area with thick line is 3'UTR used for RNAi construction
- Boxed area with dotted line is inserted region
- Boxed area with black background and white letters are start/stop codon
- Outlined letter is mutated site (A → T)

FIG. 5A

5' UTR - coding region - 3' UTR

```
     5'
   1 tcggatgatcctcaccgcactttcaatagagtaaatagttgtccaagacacgaagaagat  60

61 aacggtactttatgcttctgtatctttagagagagttccacttctacattgtaacctgtg 120

121 actttgagagtgtttgttccattgttgttgtagaaaaaccatctcaaagctgagaaatga 180

181 aacgactcggttcattggttgaagtctaaaccggtataaaatcccggttttaatctaatc 240

241 tagaccaaaccgtgtttcttatatatatttgaatccgtgatttacgcacgactggttaaa 300
                                            T -change to eliminate SacI site
 301 gcagaATGGAATCAAAATCAGAACAAAACGAGTGGAGCTCCGGCGTGTGGGCTCACTTAA 360
         M  E  S  K  S  Q  N  E  W  S  S  G  V  W  A  H  L  T -

361 CCGCCGTACGGCAACAATCGCCGCTTGTTCAGTGCATCACCAACTTCGTCTCGATGGATC 420
      A  V  R  Q  Q  S  P  L  V  Q  C  I  T  N  F  V  S  M  D  L -

421 TCGTTGCCAACACGCTTTTATCCGCCGGTGCATCTCCAGCGATGGTCCATTCCGTCGTTG 480
      V  A  N  T  L  L  S  A  G  A  S  P  A  M  V  H  S  V  V  E -

481 AGATTCCTGATTTCACTCCTCATATTCACGCGCTCTGCGTCAACGTCGGAACACTTACAC 540
      I  P  D  F  T  P  H  I  H  A  L  C  V  N  V  G  T  L  T  P -

541 CTGACTGGCTTCCGTCAATGAAAGCTGCCGCTGAACTCGCTTCTCAGCTCCGAAAGCCTT 600
      D  W  L  P  S  M  K  A  A  A  E  L  A  S  Q  L  R  K  P  W -

601 GGGTTCTTGATCCCGCCGCCGTGAGTTGCTCCGGATTCCGATTAAAAGCGTGTTTGGAGC 660
      V  L  D  P  A  A  V  S  C  S  G  F  R  L  K  A  C  L  E  L -

661 TCATCGAGCTAAAACCTACTGTAATCAAAGGAAACGGTTCTGAGATTATTGCTCTCTCCT 720
      I  E  L  K  P  T  V  I  K  G  N  G  S  E  I  I  A  L  S  S -

721 CTGCTTCACGTGGACAAACTAAGGGTGCTGATAGCTCACATGAATCAACAGACGCTATAG 780
      A  S  R  G  Q  T  K  G  A  D  S  S  H  E  S  T  D  A  I  E -

781 AAGCTGCAAAGTCATTAGCGATGTCAAGTGGTGCTGTTGTTGCAGTGTCAGGAGCTGTTG 840
      A  A  K  S  L  A  M  S  S  G  A  V  V  A  V  S  G  A  V  D -

841 ATATTGTTACTGATGGGAAACAGGTTATTGGTGTTCACAACGGGACGAAGATGATGCAAC 900
      I  V  T  D  G  K  Q  V  I  G  V  H  N  G  T  K  M  M  Q  Q -

901 AGATTACTGCAACTGGTTGTTCTCTAGCTGGTTTGATTGTAGCGTTTCTTGCTATTGATT 960
      I  T  A  T  G  C  S  L  A  G  L  I  V  A  F  L  A  I  D  S -
```

FIG. 5B

```
961  CATCACGGGTACTGGAAGCTACGGTTTCCGCTATGGCTGTCTTTGGCATTGCAGGTGAGT 1020
      S  R  V  L  E  A  T  V  S  A  M  A  V  F  G  I  A  G  E  L  -

1021 TGGGTGAAGCGATGGCGAATGGTCCAGCGTCATTGAGAATGCATTTGATAGATTGTCTTT 1080
      G  E  A  M  A  N  G  P  A  S  L  R  M  H  L  I  D  C  L  Y  -

1081 ATGGGTTGGATGAAACCACAGTGCTTAAACGTGTGAATGTGACCAGGTTGGGT TGA tgta 1140
      G  L  D  E  T  T  V  L  K  R  V  N  V  T  R  L  G  *

1141 catgaatcatcttctttgaataaagtttcttaagatatctctgcaatttttcttgatcatt 1200
            Boxed sequence used to make Thi3-RNAi construct
1201 agtatatcgtccagcttcaggtagataggagtgtcatggttatatagcttttgtggtcac 1260

1261 catcttagactttaaggcaatgttcaaaaattacactttaacaatcttagaagtttcat 1320

1321 ggctttggatgatttg ctttcgatcaataactgttacatacaacaacaaaagaacattca 1380

1381 cacacacgcacacatgtagaaatttgaaatcttttggtaaggctacttttgggttttgt 1439
                                                              3'
```

FIG. 6A

```
  1 ATGGACACTAAGATCGGATCTATCGACGCGTGTAACCCGACCAACCACGATATCGGCGGT  60
    M  D  T  K  I  G  S  I  D  A  C  N  P  T  N  H  D  I  G  G  -

61 CCTCCAAACGGCGGAGTCTCCACCGTTCAAAACACAAGTCCACTTCACTCCACCACCGTC 120
    P  P  N  G  G  V  S  T  V  Q  N  T  S  P  L  H  S  T  T  V  -

121 AGCCCCTGCGACGCGACTCTTGGCCGTTACCTAGCAAGACGGTTAGTCGAAATCGGCGTC 180
    S  P  C  D  A  T  L  G  R  Y  L  A  R  R  L  V  E  I  G  V  -

181 ACCGATGTCTTCTCCGTTCCTGGTGATTTCAACCTGACGCTTCTCGATCACCTAATCGCC 240
    T  D  V  F  S  V  P  G  D  F  N  L  T  L  L  D  H  L  I  A  -

241 GAACCAAACCTCAAGCTGATCGGTTGCTGCAACGAGCTTAACGCCGGATACGCTGCTGAC 300
    E  P  N  L  K  L  I  G  C  C  N  E  L  N  A  G  Y  A  A  D  -

301 GGTTACGCTAGATCTCGCGGTGTTGGTGCGTGCGTCGTTACGTTCACCGTCGGTGGATTG 360
    G  Y  A  R  S  R  G  V  G  A  C  V  V  T  F  T  V  G  G  L  -

361 AGTGTTCTGAATGCGATCGCCGGTGCTTACAGTGAGAATCTGCCTCTGATTTGCATCGTC 420
    S  V  L  N  A  I  A  G  A  Y  S  E  N  L  P  L  I  C  I  V  -

421 GGTGGTCCAAACTCCAACGATTACGGTACCAATAGGATTCTTCATCATACAATTGGTTTA 480
    G  G  P  N  S  N  D  Y  G  T  N  R  I  L  H  H  T  I  G  L  -

481 CCTGATTTCACTCAAGAGCTTAGGTGTTTTCAAGCTGTTACTTGTTTTCAAGCTGTGATT 540
    P  D  F  T  Q  E  L  R  C  F  Q  A  V  T  C  F  Q  A  V  I  -

541 AATAACTTAGAAGAGGCTCATGAACTTATCGATACTGCGATTTCAACTGCTTTGAAAGAA 600
    N  N  L  E  E  A  H  E  L  I  D  T  A  I  S  T  A  L  K  E  -

601 AGCAAACCTGTTTATATCAGTATCAGCTGTAATTTACCGGCGATTCCTCTTCCGACGTTT 660
    S  K  P  V  Y  I  S  I  S  C  N  L  P  A  I  P  L  P  T  F  -

661 AGTCGTCATCCTGTTCCGTTCATGCTTCCGATGAAGGTTAGCAATCAGATTGGTTTAGAT 720
    S  R  H  P  V  P  F  M  L  P  M  K  V  S  N  Q  I  G  L  D  -

721 GCGGCGGTGGAGGCAGCTGCTGAGTTCTTGAACAAAGCTGTGAAGCCAGTTCTTGTTGGT 780
    A  A  V  E  A  A  A  E  F  L  N  K  A  V  K  P  V  L  V  G  -

781 GGGCCGAAAATGCGGGTTGCGAAAGCCGCGGATGCTTTTGTTGAGCTTGCTGATGCTTCT 840
    G  P  K  M  R  V  A  K  A  A  D  A  F  V  E  L  A  D  A  S  -

841 GGCTATGGTCTTGCTGTGATGCCTTCTGCTAAAGGACAAGTACCTGAGCATCACAAGCAT 900
    G  Y  G  L  A  V  M  P  S  A  K  G  Q  V  P  E  H  H  K  H  -

901 TTTATAGGGACGTATTGGGGAGCTGTGAGTACAGCTTTTTGTGCTGAAATCGTTGAATCT 960
    F  I  G  T  Y  W  G  A  V  S  T  A  F  C  A  E  I  V  E  S  -

961 GCGGATGCTTATCTGTTTGCAGGTCCGATTTTCAACGATTACAGTTCTGTTGGGTATTCT 1020
    A  D  A  Y  L  F  A  G  P  I  F  N  D  Y  S  S  V  G  Y  S  -

1021 CTGCTTCTCAAGAAGGAGAAGGCAATCATCGTTCAGCCTGATCGGGTTACTATCGGTAAC 1080
     L  L  L  K  K  E  K  A  I  I  V  Q  P  D  R  V  T  I  G  N  -

1081 GGACCTGCGTTTGGATGTGTTCTTATGAAGGATTTTCTAAGCGAGTTGGCTAAACGAATT 1140
     G  P  A  F  G  C  V  L  M  K  D  F  L  S  E  L  A  K  R  I  -

1141 AAGCACAACAACACTTCTTATGAGAATTATCACAGGATCTATGTCCCAGAAGGAAAGCCT 1200
     K  H  N  N  T  S  Y  E  N  Y  H  R  I  Y  V  P  E  G  K  P  -
```

FIG. 6B

```
1201 TTGAGAGATAACCCGAATGAGTCTTTGAGGGTTAATGTACTGTTCCAACACATTCAGAAT 1260
      L  R  D  N  P  N  E  S  L  R  V  N  V  L  F  Q  H  I  Q  N  -

1261 ATGCTCTCTTCTGAGTCTGCTGTGCTTGCTGAGACAGGAGATTCCTGGTTCAACTGTCAG 1320
      M  L  S  S  E  S  A  V  L  A  E  T  G  D  S  W  F  N  C  Q  -

1321 AAGCTGAAGCTCCCTGAAGGATGCGGTTACGAATTCCAAATGCAGTACGGATCAATTGGC 1380
      K  L  K  L  P  E  G  C  G  Y  E  F  Q  M  Q  Y  G  S  I  G  -

1381 TGGTCAGTGGGTGCTACTCTAGGCTATGCTCAAGCCATGCCAAACAGGCGTGTCATTGCT 1440
      W  S  V  G  A  T  L  G  Y  A  Q  A  M  P  N  R  R  V  I  A  -

1441 TGTATTGGAGATGGTAGTTTCCAGGTAACCGCACAGGATGTATCTACGATGATACGGTGT 1500
      C  I  G  D  G  S  F  Q  V  T  A  Q  D  V  S  T  M  I  R  C  -

1501 GGGCAAAAGACCATAATCTTCCTCATCAACAACGGAGGCTACACCATT GAG GTGGAAATT 1560    CAA
      G  Q  K  T  I  I  F  L  I  N  N  G  G  Y  T  I  E  V  E  I  -       Q

1561 CACGATGGTCCTTACAATGTCATAAAGAACTGGAACTACACAGCTTTTGTTGAGGCCATA 1620
      H  D  G  P  Y  N  V  I  K  N  W  N  Y  T  A  F  V  E  A  I  -

1621 CACAATGGAGAAGGAAAATGCTGGACTGCCAAGGTGAGATGCGAGGAGGAGTTAGTGAAA 1680
      H  N  G  E  G  K  C  W  T  A  K  V  R  C  E  E  E  L  V  K  -

1681 GCAATCAACACGGCAACCAATGAGGAAAAAGAGAGCTTTTGTTTCATTGAAGTGATAGTG 1740
      A  I  N  T  A  T  N  E  E  K  E  S  F  C  F  I  E  V  I  V  -

1741 CACAAAGACGATACAAGCAAGGAACTTTTGGAGTGGGGCTCTAGAGTCTCTGCTGCTAAT 1800
      H  K  D  D  T  S  K  E  L  L  E  W  G  S  R  V  S  A  A  N  -

1801 AGTCGTCCCCCAAATCCGCAG TAG 1824
      S  R  P  P  N  P  Q  *  -
```

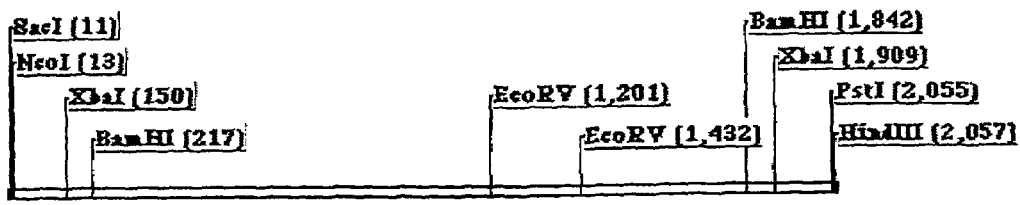

- Primer sets

AtThi2i-v2S1

<u>TTT CTT GCC GTT TTC GTC GGT A</u>TA GAT TCG TAC TTG TTA AAG GT    (SEQ ID NO:15)

AtThi2i-v2SacNcoA1

TGA TAG TGA TAG TGA TAG TGA GAC CTC CCA TGG GAC CGG CAT ATA TCA ATG CAT GCT TTT    (SEQ ID NO:16)

AtThi2i-v2S2

<u>ACT GGA AAA AGA ACT TCT GGC CT</u>T AGA TTC GTA CTT GTT AAA GGT    (SEQ ID NO:17)

AtThi2i-v2PstHindA2

AGC GTT AGC GTT AGC GTT AGC AAG CTT CTG CAT GAC CGG CAT ATA TCA ATG CAT GCT TTT    (SEQ ID NO:18)

FIG. 8

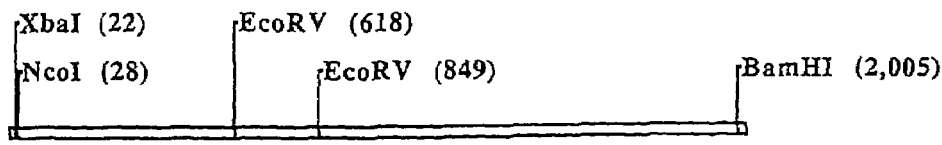

- Primer sets

AtThi3i-v2S1

<u>TTT CTT GCC GTT TTC GTC GGT AAG</u> CTC ATC GAG CTA AAA CCT ACT GTA A  (SEQ ID NO:19)

AtThi3i-v2S2

<u>ACT GGA AAA AGA ACT TCT GGC CTA</u> GCT CAT CGA GCT AAA ACC TAC TGT AA  (SEQ ID NO:20)

AtThi3i-v2XbaNcoA1

<u>TGA TAG TGA TAG TGA TAG TGA</u> TCT AGA CCA TGG CAA CCT GGT CAC ATT CAC ACG TTT AA
(SEQ ID NO:21)

AtThi3i-v2BamA2

<u>AGC GTT AGC GTT AGC GTT AGC</u> GGA TCC CAA CCT GGT CAC ATT CAC ACG TTT AA  (SEQ ID NO:22)

FIG. 9

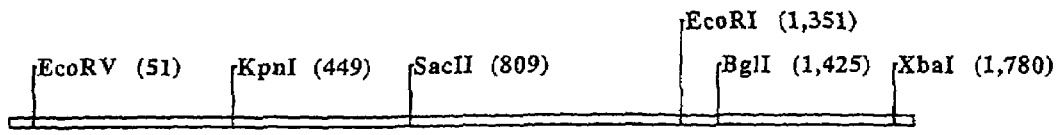

Mapping all cutsites.

Cutters : BglI, EcoRI, EcoRV, KpnI, SacII & XbaI

Non-Cutters : ApaI, BamHI, HindIII, NcoI, NotI, PstI, SacI, SalI, SmaI, SpeI & XhoI

- Primer sets

AtPDC2SacNcoS1

TAG AGT GAG CTC CCA TGG ACA CTA AGA TCG GAT CTA TCG ACG GCT GTA    (SEQ ID NO:23)

AtPDC2A1

ATT GTA AGG ACC ATC GTG AAT TTC CAC ATG AAT GGT GTA GCC TCC GTT GTT GAT    (SEQ ID NO:24)

AtPDC2S1

ATC AAC AAC GGA GGC TAC ACC ATT CAG GTG AAA ATT CAC GAT GGT CCT TAC AAT    (SEQ ID NO:25)

AtPDC2BamA2

TTC GAT GGA TCC CTA CTG CGG ATT TGG GGG ACG ACT ATT AGC AGC AGA    (SEQ ID NO:26)

FIG. 10

SEQUENCE LISTING

<160> NUMBER OF SEQ ID NOS: 26

<210> SEQ ID NO 1
<211> LENGTH: 2492
<212> TYPE: DNA
<213> ORGANISM: Arabidopsis thaliana
<220> FEATURE:
<221> NAME/KEY: CDS
<222> LOCATION: (590)..(2110)

<400> SEQUENCE: 1

```
accaaaccaa accactcggt aaacttgtat agcctcttgt atatattatg atatatatca      60
ataataatta cacgtgtaat gtaagatgca ttttgatttg aagatgcatt atgctgattt     120
gtaaaacata aacggctttg gtccctttt agtgtgtccg aatgaataag gtgttcaaaa     180
tagcgtgtga tttgtaattt gtaatttgta attagtctga aacgttgtat atatgaatat     240
tcttcaatta tataaaagct tgctttcaaa tatatcaatt tatctatctt ttgattatat     300
tgtccctttt tcgtggacca caagtattaa cttatctcat acaaataatt cgtgcttaag     360
tttggtgtta aaattattga aaattgattt acattgaatt ttttttcgcgg taattgataa    420 ttcatgaaaa tcgatgaaat ttactaattt tatttcacat taaagtcaat aaaatgggaa    480
aatatttgat gagaataaaa taaaataaaa taaagagaag ggacgagaaa tgaatagctt     540
aggaggaatt aggagttggc cggcgaattg gagaagtacg acggcgtca atg gga acg     598
                                                        Met Gly Thr
                                                          1 acg acg gag agc gtt aga aag gtt ccg caa gtt tta aca gtg gcg gga       646
Thr Thr Glu Ser Val Arg Lys Val Pro Gln Val Leu Thr Val Ala Gly
          5                  10                  15 tca gat tcc ggc gcc gga gct gga att caa gcc gac ctt aaa gtc tgc       694
Ser Asp Ser Gly Ala Gly Ala Gly Ile Gln Ala Asp Leu Lys Val Cys
 20                  25                  30                  35 gca gct cgt ggt gtg tat tgc gct tcc gtc ata acc gca gtc act gct       742
Ala Ala Arg Gly Val Tyr Cys Ala Ser Val Ile Thr Ala Val Thr Ala
                 40                  45                  50 cag aac act cga gga gtt caa tct gtt cat ctt ctt cct ccg gaa ttt       790
Gln Asn Thr Arg Gly Val Gln Ser Val His Leu Leu Pro Pro Glu Phe
             55                  60                  65 atc tct gaa cag ctc aaa tcc gtc ctc tct gac ttc gaa ttc gac gtc       838
Ile Ser Glu Gln Leu Lys Ser Val Leu Ser Asp Phe Glu Phe Asp Val
         70                  75                  80 gtg aag act ggg atg ctt cct tct act gag atc gtt gag gtt ctt ctt       886
Val Lys Thr Gly Met Leu Pro Ser Thr Glu Ile Val Glu Val Leu Leu
 85                  90                  95 caa aat cta tca gat ttt cca gtt cgt ggt aga gat tac ctc gct ttg       934
Gln Asn Leu Ser Asp Phe Pro Val Arg Gly Arg Asp Tyr Leu Ala Leu
100                 105                 110                 115 ttc tct ttg gtt gtt gat cct gtg atg gta tct act agt ggt cac gtt       982
Phe Ser Leu Val Val Asp Pro Val Met Val Ser Thr Ser Gly His Val
                120                 125                 130 ttg gct ggt tct tct att ctc tct atc ttt aga gag aga tta cta cca      1030
Leu Ala Gly Ser Ser Ile Leu Ser Ile Phe Arg Glu Arg Leu Leu Pro
            135                 140                 145 att gct gac ata att acc cca aat gtg aaa gag gct tct gct tta ctt      1078
Ile Ala Asp Ile Ile Thr Pro Asn Val Lys Glu Ala Ser Ala Leu Leu
        150                 155                 160 gat ggt ttt cgg att gag act gtt gca gaa atg cgg tct gca gca aag      1126
Asp Gly Phe Arg Ile Glu Thr Val Ala Glu Met Arg Ser Ala Ala Lys
```

```
            165                 170                 175
tcg ttg cat gaa atg ggt cct aga ttc gta ctt gtt aaa ggt ggt gat         1174
Ser Leu His Glu Met Gly Pro Arg Phe Val Leu Val Lys Gly Gly Asp
180                 185                 190                 195 ctt cct gac tca tca gat tca gta gat gtt tac ttt gat ggc aag gag         1222
Leu Pro Asp Ser Ser Asp Ser Val Asp Val Tyr Phe Asp Gly Lys Glu
                200                 205                 210 ttt cat gaa ctc cgt tct cct cgc ata gct aca aga aat act cat ggg         1270
Phe His Glu Leu Arg Ser Pro Arg Ile Ala Thr Arg Asn Thr His Gly
            215                 220                 225 act ggt tgc act ttg gct tcc tgt att gca gct gag ctt gca aaa ggc         1318
Thr Gly Cys Thr Leu Ala Ser Cys Ile Ala Ala Glu Leu Ala Lys Gly
        230                 235                 240 tct tcc atg ctc tca gcc gtc aag gtg gct aaa cgc ttt gtc gat aat         1366
Ser Ser Met Leu Ser Ala Val Lys Val Ala Lys Arg Phe Val Asp Asn
    245                 250                 255 gcc cta gat tac agc aaa gat att gtc att ggc agt ggg atg caa gga         1414
Ala Leu Asp Tyr Ser Lys Asp Ile Val Ile Gly Ser Gly Met Gln Gly
260                 265                 270                 275 cct ttt gac cat ttt ttt ggt ctt aag aag gat cct caa agt tct cga         1462
Pro Phe Asp His Phe Phe Gly Leu Lys Lys Asp Pro Gln Ser Ser Arg
                280                 285                 290 tgc agc ata ttc aat cca gat gac ctg ttt cta tat gct gtt aca gat         1510
Cys Ser Ile Phe Asn Pro Asp Asp Leu Phe Leu Tyr Ala Val Thr Asp
            295                 300                 305 tct aga atg aac aaa aaa tgg aac cgt tcc att gtg gat gcc ttg aaa         1558
Ser Arg Met Asn Lys Lys Trp Asn Arg Ser Ile Val Asp Ala Leu Lys
        310                 315                 320 gct gct ata gag gga ggg gcc acc atc ata caa ctg agg ttt gat cat         1606
Ala Ala Ile Glu Gly Gly Ala Thr Ile Ile Gln Leu Arg Phe Asp His
    325                 330                 335 ttt ctt gaa gaa gca aaa gca tgc att gat ata tgc cgg tcc cat gga         1654
Phe Leu Glu Glu Ala Lys Ala Cys Ile Asp Ile Cys Arg Ser His Gly
340                 345                 350                 355 gtt agt ttg ctg ata aac gac agg atc gac att gcc ctt gct tgt gat         1702
Val Ser Leu Leu Ile Asn Asp Arg Ile Asp Ile Ala Leu Ala Cys Asp
                360                 365                 370 gct gat gga gtc cat gtt ggt caa tcc gac atg ccg gtt gat cta gtt         1750
Ala Asp Gly Val His Val Gly Gln Ser Asp Met Pro Val Asp Leu Val
            375                 380                 385 cgg tct ctt ctt ggc ccg gac aag atc ata ggg gtc tca tgt aag aca         1798
Arg Ser Leu Leu Gly Pro Asp Lys Ile Ile Gly Val Ser Cys Lys Thr
        390                 395                 400 cca gaa caa gct cat caa gca tgg aaa gat ggt gcg gac tac att ggg         1846
Pro Glu Gln Ala His Gln Ala Trp Lys Asp Gly Ala Asp Tyr Ile Gly
    405                 410                 415 tca gga gga gtt ttt cca acg aac act aag gcc aac aat cgt acc ata         1894
Ser Gly Gly Val Phe Pro Thr Asn Thr Lys Ala Asn Asn Arg Thr Ile
420                 425                 430                 435 gga ctt gat ggg cta aaa gaa gta tgt gaa gca tca aaa tta ccg gtt         1942
Gly Leu Asp Gly Leu Lys Glu Val Cys Glu Ala Ser Lys Leu Pro Val
                440                 445                 450 gtt gca atc gga ggc ata ggg atc tca aat gct ggg tct gtt atg cag         1990
Val Ala Ile Gly Gly Ile Gly Ile Ser Asn Ala Gly Ser Val Met Gln
            455                 460                 465 atc gat gca ccg aac cta aaa ggt gta gca gtt gtg tca gct ttg ttc         2038
Ile Asp Ala Pro Asn Leu Lys Gly Val Ala Val Val Ser Ala Leu Phe
        470                 475                 480 gac caa gat tgt gtt ttg act caa gct aag aag ttg cat aaa acg ctt         2086
```

```
Asp Gln Asp Cys Val Leu Thr Gln Ala Lys Lys Leu His Lys Thr Leu
    485                 490                 495 aaa gag agc aaa agg gga att tga accaaaggt gttttagtt ttgttttagg      2140
Lys Glu Ser Lys Arg Gly Ile
500             505 tgcttacaaa atgttgtaaa cctttactt cttacttga tgtattttt tttttttt       2200 gagaaagcca gaaagataa atagtaatga ttgctacaaa cattttact tccaaaaact     2260 tccaacattc tcaaattctc caagagataa catttgtgta tttcatttgc cttcactcct   2320
ctaagaaatt tattgttaca ggcagcaatc tgaaaaatgg aacaaaattt acctttgaca   2380
aaggtatcta atgcttgctt acaaacaaac gatttaactt gcctctctat atacacatag   2440
ccactggaat ggtacaaaga agatgaggta tttgacatat tcttgttttt gt           2492

<210> SEQ ID NO 2
<211> LENGTH: 506
<212> TYPE: PRT
<213> ORGANISM: Arabidopsis thaliana

<400> SEQUENCE: 2

Met Gly Thr Thr Thr Glu Ser Val Arg Lys Val Pro Gln Val Leu Thr
1               5                   10                  15

Val Ala Gly Ser Asp Ser Gly Ala Gly Ala Gly Ile Gln Ala Asp Leu
            20                  25                  30

Lys Val Cys Ala Ala Arg Gly Val Tyr Cys Ala Ser Val Ile Thr Ala
        35                  40                  45

Val Thr Ala Gln Asn Thr Arg Gly Val Gln Ser Val His Leu Leu Pro
    50                  55                  60

Pro Glu Phe Ile Ser Glu Gln Leu Lys Ser Val Leu Ser Asp Phe Glu
65                  70                  75                  80

Phe Asp Val Val Lys Thr Gly Met Leu Pro Ser Thr Glu Ile Val Glu
                85                  90                  95

Val Leu Leu Gln Asn Leu Ser Asp Phe Pro Val Arg Gly Arg Asp Tyr
            100                 105                 110

Leu Ala Leu Phe Ser Leu Val Val Asp Pro Val Met Val Ser Thr Ser
        115                 120                 125

Gly His Val Leu Ala Gly Ser Ser Ile Leu Ser Ile Phe Arg Glu Arg
    130                 135                 140

Leu Leu Pro Ile Ala Asp Ile Ile Thr Pro Asn Val Lys Glu Ala Ser
145                 150                 155                 160

Ala Leu Leu Asp Gly Phe Arg Ile Glu Thr Val Ala Glu Met Arg Ser
                165                 170                 175

Ala Ala Lys Ser Leu His Glu Met Gly Pro Arg Phe Val Leu Val Lys
            180                 185                 190

Gly Gly Asp Leu Pro Asp Ser Ser Asp Ser Val Asp Val Tyr Phe Asp
        195                 200                 205

Gly Lys Glu Phe His Glu Leu Arg Ser Pro Arg Ile Ala Thr Arg Asn
    210                 215                 220

Thr His Gly Thr Gly Cys Thr Leu Ala Ser Cys Ile Ala Ala Glu Leu
225                 230                 235                 240

Ala Lys Gly Ser Ser Met Leu Ser Ala Val Lys Val Ala Lys Arg Phe
                245                 250                 255

Val Asp Asn Ala Leu Asp Tyr Ser Lys Asp Ile Val Ile Gly Ser Gly
            260                 265                 270

Met Gln Gly Pro Phe Asp His Phe Phe Gly Leu Lys Lys Asp Pro Gln
```

```
                275                 280                 285
Ser Ser Arg Cys Ser Ile Phe Asn Pro Asp Asp Leu Phe Leu Tyr Ala
        290                 295                 300

Val Thr Asp Ser Arg Met Asn Lys Lys Trp Asn Arg Ser Ile Val Asp
305                 310                 315                 320

Ala Leu Lys Ala Ala Ile Glu Gly Gly Ala Thr Ile Ile Gln Leu Arg
                325                 330                 335

Phe Asp His Phe Leu Glu Ala Lys Ala Cys Ile Asp Ile Cys Arg
                340                 345                 350

Ser His Gly Val Ser Leu Leu Ile Asn Asp Arg Ile Asp Ile Ala Leu
                355                 360                 365

Ala Cys Asp Ala Asp Gly Val His Val Gly Gln Ser Asp Met Pro Val
        370                 375                 380

Asp Leu Val Arg Ser Leu Leu Gly Pro Asp Lys Ile Ile Gly Val Ser
385                 390                 395                 400

Cys Lys Thr Pro Glu Gln Ala His Gln Ala Trp Lys Asp Gly Ala Asp
                405                 410                 415

Tyr Ile Gly Ser Gly Gly Val Phe Pro Thr Asn Thr Lys Ala Asn Asn
                420                 425                 430

Arg Thr Ile Gly Leu Asp Gly Leu Lys Glu Val Cys Glu Ala Ser Lys
                435                 440                 445

Leu Pro Val Val Ala Ile Gly Gly Ile Gly Ile Ser Asn Ala Gly Ser
        450                 455                 460

Val Met Gln Ile Asp Ala Pro Asn Leu Lys Gly Val Ala Val Val Ser
465                 470                 475                 480

Ala Leu Phe Asp Gln Asp Cys Val Leu Thr Gln Ala Lys Lys Leu His
                485                 490                 495

Lys Thr Leu Lys Glu Ser Lys Arg Gly Ile
                500                 505

<210> SEQ ID NO 3
<211> LENGTH: 1439
<212> TYPE: DNA
<213> ORGANISM: Arabidopsis thaliana
<220> FEATURE:
<221> NAME/KEY: CDS
<222> LOCATION: (306)..(1136)

<400> SEQUENCE: 3
tcggatgatc ctcaccgcac tttcaataga gtaaatagtt gtccaagaca cgaagaagat      60
aacggtactt tatgcttctg tatctttaga gagagttcca cttctacatt gtaacctgtg     120
actttgagag tgtttgttcc attgttgttg tagaaaaacc atctcaaagc tgagaaatga     180
aacgactcgg ttcattggtt gaagtctaaa ccggtataaa atcccggttt taatctaatc     240
tagaccaaac cgtgtttctt atatatattt gaatccgtga tttacgcacg actggttaaa     300 gcaga atg gaa tca aaa tca gaa caa aac gag tgg agc tcc ggc gtg tgg     350
      Met Glu Ser Lys Ser Glu Gln Asn Glu Trp Ser Ser Gly Val Trp
      1               5                  10                  15 gct cac tta acc gcc gta cgg caa caa tcg ccg ctt gtt cag tgc atc     398
Ala His Leu Thr Ala Val Arg Gln Gln Ser Pro Leu Val Gln Cys Ile
                20                  25                  30 acc aac ttc gtc tcg atg gat ctc gtt gcc aac acg ctt tta tcc gcc     446
Thr Asn Phe Val Ser Met Asp Leu Val Ala Asn Thr Leu Leu Ser Ala
            35                  40                  45 ggt gca tct cca gcg atg gtc cat tcc gtc gtt gag att cct gat ttc     494
Gly Ala Ser Pro Ala Met Val His Ser Val Val Glu Ile Pro Asp Phe
```

|  |  |  |  |  |  |  |  |  |  |  |  |  |  |  |  |
|---|---|---|---|---|---|---|---|---|---|---|---|---|---|---|---|

```
                       50                  55                  60
act cct cat att cac gcg ctc tgc gtc aac gtc gga aca ctt aca cct      542
Thr Pro His Ile His Ala Leu Cys Val Asn Val Gly Thr Leu Thr Pro
         65                  70                  75 gac tgg ctt ccg tca atg aaa gct gcc gct gaa ctc gct tct cag ctc      590
Asp Trp Leu Pro Ser Met Lys Ala Ala Ala Glu Leu Ala Ser Gln Leu
 80                  85                  90                  95 cga aag cct tgg gtt ctt gat ccc gcc gcc gtg agt tgc tcc gga ttc      638
Arg Lys Pro Trp Val Leu Asp Pro Ala Ala Val Ser Cys Ser Gly Phe
                    100                 105                 110 cga tta aaa gcg tgt ttg gag ctc atc gag cta aaa cct act gta atc      686
Arg Leu Lys Ala Cys Leu Glu Leu Ile Glu Leu Lys Pro Thr Val Ile
            115                 120                 125 aaa gga aac ggt tct gag att att gct ctc tcc tct gct tca cgt gga      734
Lys Gly Asn Gly Ser Glu Ile Ile Ala Leu Ser Ser Ala Ser Arg Gly
        130                 135                 140 caa act aag ggt gct gat agc tca cat gaa tca aca gac gct ata gaa      782
Gln Thr Lys Gly Ala Asp Ser Ser His Glu Ser Thr Asp Ala Ile Glu
    145                 150                 155 gct gca aag tca tta gcg atg tca agt ggt gct gtt gtt gca gtg tca      830
Ala Ala Lys Ser Leu Ala Met Ser Ser Gly Ala Val Val Ala Val Ser
160                 165                 170                 175 gga gct gtt gat att gtt act gat ggg aaa cag gtt att ggt gtt cac      878
Gly Ala Val Asp Ile Val Thr Asp Gly Lys Gln Val Ile Gly Val His
                    180                 185                 190 aac ggg acg aag atg atg caa cag att act gca act ggt tgt tct cta      926
Asn Gly Thr Lys Met Met Gln Gln Ile Thr Ala Thr Gly Cys Ser Leu
            195                 200                 205 gct ggt ttg att gta gcg ttt ctt gct att gat tca tca cgg gta ctg      974
Ala Gly Leu Ile Val Ala Phe Leu Ala Ile Asp Ser Ser Arg Val Leu
        210                 215                 220 gaa gct acg gtt tcc gct atg gct gtc ttt ggc att gca ggt gag ttg     1022
Glu Ala Thr Val Ser Ala Met Ala Val Phe Gly Ile Ala Gly Glu Leu
    225                 230                 235 ggt gaa gcg atg gcg aat ggt cca gcg tca ttg aga atg cat ttg ata     1070
Gly Glu Ala Met Ala Asn Gly Pro Ala Ser Leu Arg Met His Leu Ile
240                 245                 250                 255 gat tgt ctt tat ggg ttg gat gaa acc aca gtg ctt aaa cgt gtg aat     1118
Asp Cys Leu Tyr Gly Leu Asp Glu Thr Thr Val Leu Lys Arg Val Asn
                    260                 265                 270 gtg acc agg ttg ggt tga tgtacatgaa tcatcttctt tgaataaagt            1166
Val Thr Arg Leu Gly
            275 ttcttaagat atctctgcaa ttttcttgat cattagtata tcgtccagct tcaggtagat   1226 aggagtgtca tggttatata gctttgtgg tcaccatctt agactttaag gcaatgttca    1286 aaaattacac ttttaacaat cttagaagtt tcatggcttt ggatgatttg ctttcgatca   1346 ataactgtta catacaacaa caaaagaaca ttcacacaca cgcacacatg tagaaatttg   1406 aaatctttg gtaaggctac ttttgggttt tgt                                 1439

<210> SEQ ID NO 4
<211> LENGTH: 276
<212> TYPE: PRT
<213> ORGANISM: Arabidopsis thaliana

<400> SEQUENCE: 4

Met Glu Ser Lys Ser Glu Gln Asn Glu Trp Ser Ser Gly Val Trp Ala
 1               5                  10                  15
```

```
His Leu Thr Ala Val Arg Gln Gln Ser Pro Leu Val Gln Cys Ile Thr
            20                  25                  30

Asn Phe Val Ser Met Asp Leu Ala Asn Thr Leu Leu Ser Ala Gly
        35                  40                  45

Ala Ser Pro Ala Met Val His Ser Val Val Glu Ile Pro Asp Phe Thr
 50                  55                  60

Pro His Ile His Ala Leu Cys Val Asn Val Gly Thr Leu Thr Pro Asp
 65                  70                  75                  80

Trp Leu Pro Ser Met Lys Ala Ala Glu Leu Ala Ser Gln Leu Arg
                85                  90                  95

Lys Pro Trp Val Leu Asp Pro Ala Ala Val Ser Cys Ser Gly Phe Arg
            100                 105                 110

Leu Lys Ala Cys Leu Glu Leu Ile Glu Leu Lys Pro Thr Val Ile Lys
        115                 120                 125

Gly Asn Gly Ser Glu Ile Ile Ala Leu Ser Ser Ala Ser Arg Gly Gln
130                 135                 140

Thr Lys Gly Ala Asp Ser Ser His Glu Ser Thr Asp Ala Ile Glu Ala
145                 150                 155                 160

Ala Lys Ser Leu Ala Met Ser Ser Gly Ala Val Val Ala Val Ser Gly
            165                 170                 175

Ala Val Asp Ile Val Thr Asp Gly Lys Gln Val Ile Gly Val His Asn
        180                 185                 190

Gly Thr Lys Met Met Gln Gln Ile Thr Ala Thr Gly Cys Ser Leu Ala
    195                 200                 205

Gly Leu Ile Val Ala Phe Leu Ala Ile Asp Ser Ser Arg Val Leu Glu
        210                 215                 220

Ala Thr Val Ser Ala Met Ala Val Phe Gly Ile Ala Gly Glu Leu Gly
225                 230                 235                 240

Glu Ala Met Ala Asn Gly Pro Ala Ser Leu Arg Met His Leu Ile Asp
            245                 250                 255

Cys Leu Tyr Gly Leu Asp Glu Thr Thr Val Leu Lys Arg Val Asn Val
        260                 265                 270

Thr Arg Leu Gly
        275

<210> SEQ ID NO 5
<211> LENGTH: 1824
<212> TYPE: DNA
<213> ORGANISM: Arabidopsis thaliana
<220> FEATURE:
<221> NAME/KEY: CDS
<222> LOCATION: (1)..(1824)

<400> SEQUENCE: 5 atg gac act aag atc gga tct atc gac gcg tgt aac ccg acc aac cac      48
Met Asp Thr Lys Ile Gly Ser Ile Asp Ala Cys Asn Pro Thr Asn His
  1               5                  10                  15 gat atc ggc ggt cct cca aac ggc gga gtc tcc acc gtt caa aac aca      96
Asp Ile Gly Gly Pro Pro Asn Gly Gly Val Ser Thr Val Gln Asn Thr
             20                  25                  30 agt cca ctt cac tcc acc acc gtc agc ccc tgc gac gcg act ctt ggc     144
Ser Pro Leu His Ser Thr Thr Val Ser Pro Cys Asp Ala Thr Leu Gly
         35                  40                  45 cgt tac cta gca aga cgg tta gtc gaa atc ggc gtc acc gat gtc ttc     192
Arg Tyr Leu Ala Arg Arg Leu Val Glu Ile Gly Val Thr Asp Val Phe
     50                  55                  60 tcc gtt cct ggt gat ttc aac ctg acg ctt ctc gat cac cta atc gcc     240
```

```
Ser Val Pro Gly Asp Phe Asn Leu Thr Leu Leu Asp His Leu Ile Ala
65                  70                  75                  80 gaa cca aac ctc aag ctg atc ggt tgc tgc aac gag ctt aac gcc gga       288
Glu Pro Asn Leu Lys Leu Ile Gly Cys Cys Asn Glu Leu Asn Ala Gly
                85                  90                  95 tac gct gct gac ggt tac gct aga tct cgc ggt gtt ggt gcg tgc gtc       336
Tyr Ala Ala Asp Gly Tyr Ala Arg Ser Arg Gly Val Gly Ala Cys Val
            100                 105                 110 gtt acg ttc acc gtc ggt gga ttg agt gtt ctg aat gcg atc gcc ggt       384
Val Thr Phe Thr Val Gly Gly Leu Ser Val Leu Asn Ala Ile Ala Gly
        115                 120                 125 gct tac agt gag aat ctg cct ctg att tgc atc gtc ggt ggt cca aac       432
Ala Tyr Ser Glu Asn Leu Pro Leu Ile Cys Ile Val Gly Gly Pro Asn
    130                 135                 140 tcc aac gat tac ggt acc aat agg att ctt cat cat aca att ggt tta       480
Ser Asn Asp Tyr Gly Thr Asn Arg Ile Leu His His Thr Ile Gly Leu
145                 150                 155                 160 cct gat ttc act caa gag ctt agg tgt ttt caa gct gtt act tgt ttt       528
Pro Asp Phe Thr Gln Glu Leu Arg Cys Phe Gln Ala Val Thr Cys Phe
                165                 170                 175 caa gct gtg att aat aac tta gaa gag gct cat gaa ctt atc gat act       576
Gln Ala Val Ile Asn Asn Leu Glu Glu Ala His Glu Leu Ile Asp Thr
            180                 185                 190 gcg att tca act gct ttg aaa gaa agc aaa cct gtt tat atc agt atc       624
Ala Ile Ser Thr Ala Leu Lys Glu Ser Lys Pro Val Tyr Ile Ser Ile
        195                 200                 205 agc tgt aat tta ccg gcg att cct ctt ccg acg ttt agt cgt cat cct       672
Ser Cys Asn Leu Pro Ala Ile Pro Leu Pro Thr Phe Ser Arg His Pro
    210                 215                 220 gtt ccg ttc atg ctt ccg atg aag gtt agc aat cag att ggt tta gat       720
Val Pro Phe Met Leu Pro Met Lys Val Ser Asn Gln Ile Gly Leu Asp
225                 230                 235                 240 gcg gcg gtg gag gca gct gct gag ttc ttg aac aaa gct gtg aag cca       768
Ala Ala Val Glu Ala Ala Ala Glu Phe Leu Asn Lys Ala Val Lys Pro
                245                 250                 255 gtt ctt gtt ggt ggg ccg aaa atg cgg gtt gcg aaa gcc gcg gat gct       816
Val Leu Val Gly Gly Pro Lys Met Arg Val Ala Lys Ala Ala Asp Ala
            260                 265                 270 ttt gtt gag ctt gct gat gct tct ggc tat ggt ctt gct gtg atg cct       864
Phe Val Glu Leu Ala Asp Ala Ser Gly Tyr Gly Leu Ala Val Met Pro
        275                 280                 285 tct gct aaa gga caa gta cct gag cat cac aag cat ttt ata ggg acg       912
Ser Ala Lys Gly Gln Val Pro Glu His His Lys His Phe Ile Gly Thr
    290                 295                 300 tat tgg gga gct gtg agt aca gct ttt tgt gct gaa atc gtt gaa tct       960
Tyr Trp Gly Ala Val Ser Thr Ala Phe Cys Ala Glu Ile Val Glu Ser
305                 310                 315                 320 gcg gat gct tat ctg ttt gca ggt ccg att ttc aac gat tac agt tct      1008
Ala Asp Ala Tyr Leu Phe Ala Gly Pro Ile Phe Asn Asp Tyr Ser Ser
                325                 330                 335 gtt ggg tat tct ctg ctt ctc aag aag gag aag gca atc atc gtt cag      1056
Val Gly Tyr Ser Leu Leu Leu Lys Lys Glu Lys Ala Ile Ile Val Gln
            340                 345                 350 cct gat cgg gtt act atc ggt aac gga cct gcg ttt gga tgt gtt ctt      1104
Pro Asp Arg Val Thr Ile Gly Asn Gly Pro Ala Phe Gly Cys Val Leu
        355                 360                 365 atg aag gat ttt cta agc gag ttg gct aaa cga att aag cac aac aac      1152
Met Lys Asp Phe Leu Ser Glu Leu Ala Lys Arg Ile Lys His Asn Asn
    370                 375                 380
```

```
act tct tat gag aat tat cac agg atc tat gtc cca gaa gga aag cct    1200
Thr Ser Tyr Glu Asn Tyr His Arg Ile Tyr Val Pro Glu Gly Lys Pro
385                 390                 395                 400 ttg aga gat aac ccg aat gag tct ttg agg gtt aat gta ctg ttc caa    1248
Leu Arg Asp Asn Pro Asn Glu Ser Leu Arg Val Asn Val Leu Phe Gln
            405                 410                 415 cac att cag aat atg ctc tct tct gag tct gct gtg ctt gct gag aca    1296
His Ile Gln Asn Met Leu Ser Ser Glu Ser Ala Val Leu Ala Glu Thr
        420                 425                 430 gga gat tcc tgg ttc aac tgt cag aag ctg aag ctc cct gaa gga tgc    1344
Gly Asp Ser Trp Phe Asn Cys Gln Lys Leu Lys Leu Pro Glu Gly Cys
    435                 440                 445 ggt tac gaa ttc caa atg cag tac gga tca att ggc tgg tca gtg ggt    1392
Gly Tyr Glu Phe Gln Met Gln Tyr Gly Ser Ile Gly Trp Ser Val Gly
450                 455                 460 gct act cta ggc tat gct caa gcc atg cca aac agg cgt gtc att gct    1440
Ala Thr Leu Gly Tyr Ala Gln Ala Met Pro Asn Arg Arg Val Ile Ala
465                 470                 475                 480 tgt att gga gat ggt agt ttc cag gta acc gca cag gat gta tct acg    1488
Cys Ile Gly Asp Gly Ser Phe Gln Val Thr Ala Gln Asp Val Ser Thr
            485                 490                 495 atg ata cgg tgt ggg caa aag acc ata atc ttc ctc atc aac aac gga    1536
Met Ile Arg Cys Gly Gln Lys Thr Ile Ile Phe Leu Ile Asn Asn Gly
        500                 505                 510 ggc tac acc att gag gtg gaa att cac gat ggt cct tac aat gtc ata    1584
Gly Tyr Thr Ile Glu Val Glu Ile His Asp Gly Pro Tyr Asn Val Ile
    515                 520                 525 aag aac tgg aac tac aca gct ttt gtt gag gcc ata cac aat gga gaa    1632
Lys Asn Trp Asn Tyr Thr Ala Phe Val Glu Ala Ile His Asn Gly Glu
530                 535                 540 gga aaa tgc tgg act gcc aag gtg aga tgc gag gag gag tta gtg aaa    1680
Gly Lys Cys Trp Thr Ala Lys Val Arg Cys Glu Glu Glu Leu Val Lys
545                 550                 555                 560 gca atc aac acg gca acc aat gag gaa aaa gag agc ttt tgt ttc att    1728
Ala Ile Asn Thr Ala Thr Asn Glu Glu Lys Glu Ser Phe Cys Phe Ile
            565                 570                 575 gaa gtg ata gtg cac aaa gac gat aca agc aag gaa ctt ttg gag tgg    1776
Glu Val Ile Val His Lys Asp Asp Thr Ser Lys Glu Leu Leu Glu Trp
        580                 585                 590 ggc tct aga gtc tct gct gct aat agt cgt ccc cca aat ccg cag tag    1824
Gly Ser Arg Val Ser Ala Ala Asn Ser Arg Pro Pro Asn Pro Gln
    595                 600                 605
```

<210> SEQ ID NO 6
<211> LENGTH: 607
<212> TYPE: PRT
<213> ORGANISM: Arabidopsis thaliana

<400> SEQUENCE: 6

```
Met Asp Thr Lys Ile Gly Ser Ile Asp Ala Cys Asn Pro Thr Asn His
1               5                   10                  15

Asp Ile Gly Gly Pro Pro Asn Gly Gly Val Ser Thr Val Gln Asn Thr
            20                  25                  30

Ser Pro Leu His Ser Thr Thr Val Ser Pro Cys Asp Ala Thr Leu Gly
        35                  40                  45

Arg Tyr Leu Ala Arg Arg Leu Val Glu Ile Gly Val Thr Asp Val Phe
    50                  55                  60

Ser Val Pro Gly Asp Phe Asn Leu Thr Leu Leu Asp His Leu Ile Ala
65                  70                  75                  80
```

```
Glu Pro Asn Leu Lys Leu Ile Gly Cys Cys Asn Glu Leu Asn Ala Gly
                 85                  90                  95

Tyr Ala Ala Asp Gly Tyr Ala Arg Ser Arg Gly Val Gly Ala Cys Val
            100                 105                 110

Val Thr Phe Thr Val Gly Gly Leu Ser Val Leu Asn Ala Ile Ala Gly
        115                 120                 125

Ala Tyr Ser Glu Asn Leu Pro Leu Ile Cys Ile Val Gly Gly Pro Asn
    130                 135                 140

Ser Asn Asp Tyr Gly Thr Asn Arg Ile Leu His His Thr Ile Gly Leu
145                 150                 155                 160

Pro Asp Phe Thr Gln Glu Leu Arg Cys Phe Gln Ala Val Thr Cys Phe
                165                 170                 175

Gln Ala Val Ile Asn Asn Leu Glu Glu Ala His Glu Leu Ile Asp Thr
            180                 185                 190

Ala Ile Ser Thr Ala Leu Lys Glu Ser Lys Pro Val Tyr Ile Ser Ile
        195                 200                 205

Ser Cys Asn Leu Pro Ala Ile Pro Leu Pro Thr Phe Ser Arg His Pro
    210                 215                 220

Val Pro Phe Met Leu Pro Met Lys Val Ser Asn Gln Ile Gly Leu Asp
225                 230                 235                 240

Ala Ala Val Glu Ala Ala Glu Phe Leu Asn Lys Ala Val Lys Pro
                245                 250                 255

Val Leu Val Gly Gly Pro Lys Met Arg Val Ala Lys Ala Ala Asp Ala
            260                 265                 270

Phe Val Glu Leu Ala Asp Ala Ser Gly Tyr Gly Leu Ala Val Met Pro
        275                 280                 285

Ser Ala Lys Gly Gln Val Pro Glu His His Lys His Phe Ile Gly Thr
    290                 295                 300

Tyr Trp Gly Ala Val Ser Thr Ala Phe Cys Ala Glu Ile Val Glu Ser
305                 310                 315                 320

Ala Asp Ala Tyr Leu Phe Ala Gly Pro Ile Phe Asn Asp Tyr Ser Ser
                325                 330                 335

Val Gly Tyr Ser Leu Leu Leu Lys Lys Glu Lys Ala Ile Ile Val Gln
            340                 345                 350

Pro Asp Arg Val Thr Ile Gly Asn Gly Pro Ala Phe Gly Cys Val Leu
        355                 360                 365

Met Lys Asp Phe Leu Ser Glu Leu Ala Lys Arg Ile Lys His Asn Asn
    370                 375                 380

Thr Ser Tyr Glu Asn Tyr His Arg Ile Tyr Val Pro Glu Gly Lys Pro
385                 390                 395                 400

Leu Arg Asp Asn Pro Asn Glu Ser Leu Arg Val Asn Val Leu Phe Gln
                405                 410                 415

His Ile Gln Asn Met Leu Ser Ser Glu Ser Ala Val Leu Ala Glu Thr
            420                 425                 430

Gly Asp Ser Trp Phe Asn Cys Gln Lys Leu Lys Leu Pro Glu Gly Cys
        435                 440                 445

Gly Tyr Glu Phe Gln Met Gln Tyr Gly Ser Ile Gly Trp Ser Val Gly
    450                 455                 460

Ala Thr Leu Gly Tyr Ala Gln Ala Met Pro Asn Arg Val Ile Ala
465                 470                 475                 480

Cys Ile Gly Asp Gly Ser Phe Gln Val Thr Ala Gln Asp Val Ser Thr
                485                 490                 495

Met Ile Arg Cys Gly Gln Lys Thr Ile Ile Phe Leu Ile Asn Asn Gly
```

-continued

```
            500                 505                 510
Gly Tyr Thr Ile Glu Val Glu Ile His Asp Gly Pro Tyr Asn Val Ile
        515                 520                 525

Lys Asn Trp Asn Tyr Thr Ala Phe Val Glu Ala Ile His Asn Gly Glu
        530                 535                 540

Gly Lys Cys Trp Thr Ala Lys Val Arg Cys Glu Glu Glu Leu Val Lys
545                 550                 555                 560

Ala Ile Asn Thr Ala Thr Asn Glu Glu Lys Glu Ser Phe Cys Phe Ile
                565                 570                 575

Glu Val Ile Val His Lys Asp Asp Thr Ser Lys Glu Leu Leu Glu Trp
            580                 585                 590

Gly Ser Arg Val Ser Ala Ala Asn Ser Arg Pro Pro Asn Pro Gln
        595                 600                 605

<210> SEQ ID NO 7
<211> LENGTH: 1824
<212> TYPE: DNA
<213> ORGANISM: Arabidopsis thaliana
<220> FEATURE:
<221> NAME/KEY: CDS
<222> LOCATION: (1)..(1824)

<400> SEQUENCE: 7 atg gac act aag atc gga tct atc gac gcg tgt aac ccg acc aac cac      48
Met Asp Thr Lys Ile Gly Ser Ile Asp Ala Cys Asn Pro Thr Asn His
1               5                   10                  15 gat atc ggc ggt cct cca aac ggc gga gtc tcc acc gtt caa aac aca      96
Asp Ile Gly Gly Pro Pro Asn Gly Gly Val Ser Thr Val Gln Asn Thr
            20                  25                  30 agt cca ctt cac tcc acc acc gtc agc ccc tgc gac gcg act ctt ggc     144
Ser Pro Leu His Ser Thr Thr Val Ser Pro Cys Asp Ala Thr Leu Gly
        35                  40                  45 cgt tac cta gca aga cgg tta gtc gaa atc ggc gtc acc gat gtc ttc     192
Arg Tyr Leu Ala Arg Arg Leu Val Glu Ile Gly Val Thr Asp Val Phe
    50                  55                  60 tcc gtt cct ggt gat ttc aac ctg acg ctt ctc gat cac cta atc gcc     240
Ser Val Pro Gly Asp Phe Asn Leu Thr Leu Leu Asp His Leu Ile Ala
65                  70                  75                  80 gaa cca aac ctc aag ctg atc ggt tgc tgc aac gag ctt aac gcc gga     288
Glu Pro Asn Leu Lys Leu Ile Gly Cys Cys Asn Glu Leu Asn Ala Gly
                85                  90                  95 tac gct gct gac ggt tac gct aga tct cgc ggt gtt ggt gcg tgc gtc     336
Tyr Ala Ala Asp Gly Tyr Ala Arg Ser Arg Gly Val Gly Ala Cys Val
            100                 105                 110 gtt acg ttc acc gtc ggt gga ttg agt gtt ctg aat gcg atc gcc ggt     384
Val Thr Phe Thr Val Gly Gly Leu Ser Val Leu Asn Ala Ile Ala Gly
        115                 120                 125 gct tac agt gag aat ctg cct ctg att tgc atc gtc ggt ggt cca aac     432
Ala Tyr Ser Glu Asn Leu Pro Leu Ile Cys Ile Val Gly Gly Pro Asn
    130                 135                 140 tcc aac gat tac ggt acc aat agg att ctt cat cat aca att ggt tta     480
Ser Asn Asp Tyr Gly Thr Asn Arg Ile Leu His His Thr Ile Gly Leu
145                 150                 155                 160 cct gat ttc act caa gag ctt agg tgt ttt caa gct gtt act tgt ttt     528
Pro Asp Phe Thr Gln Glu Leu Arg Cys Phe Gln Ala Val Thr Cys Phe
                165                 170                 175 caa gct gtg att aat aac tta gaa gag gct cat gaa ctt atc gat act     576
Gln Ala Val Ile Asn Asn Leu Glu Glu Ala His Glu Leu Ile Asp Thr
            180                 185                 190
```

| | |
|---|---|
| gcg att tca act gct ttg aaa gaa agc aaa cct gtt tat atc agt atc<br>Ala Ile Ser Thr Ala Leu Lys Glu Ser Lys Pro Val Tyr Ile Ser Ile<br>    195                        200                        205 | 624 |
| agc tgt aat tta ccg gcg att cct ctt ccg acg ttt agt cgt cat cct<br>Ser Cys Asn Leu Pro Ala Ile Pro Leu Pro Thr Phe Ser Arg His Pro<br>210                      215                      220 | 672 |
| gtt ccg ttc atg ctt ccg atg aag gtt agc aat cag att ggt tta gat<br>Val Pro Phe Met Leu Pro Met Lys Val Ser Asn Gln Ile Gly Leu Asp<br>225                      230                                240 | 720 |
| gcg gcg gtg gag gca gct gct gag ttc ttg aac aaa gct gtg aag cca<br>Ala Ala Val Glu Ala Ala Ala Glu Phe Leu Asn Lys Ala Val Lys Pro<br>                    245                      250                      255 | 768 |
| gtt ctt gtt ggt ggg ccg aaa atg cgg gtt gcg aaa gcc gcg gat gct<br>Val Leu Val Gly Gly Pro Lys Met Arg Val Ala Lys Ala Ala Asp Ala<br>                    260                      265                      270 | 816 |
| ttt gtt gag ctt gct gat gct tct ggc tat ggt ctt gct gtg atg cct<br>Phe Val Glu Leu Ala Asp Ala Ser Gly Tyr Gly Leu Ala Val Met Pro<br>                    275                      280                      285 | 864 |
| tct gct aaa gga caa gta cct gag cat cac aag cat ttt ata ggg acg<br>Ser Ala Lys Gly Gln Val Pro Glu His His Lys His Phe Ile Gly Thr<br>                    290                      295                      300 | 912 |
| tat tgg gga gct gtg agt aca gct ttt tgt gct gaa atc gtt gaa tct<br>Tyr Trp Gly Ala Val Ser Thr Ala Phe Cys Ala Glu Ile Val Glu Ser<br>305                      310                      315                      320 | 960 |
| gcg gat gct tat ctg ttt gca ggt ccg att ttc aac gat tac agt tct<br>Ala Asp Ala Tyr Leu Phe Ala Gly Pro Ile Phe Asn Asp Tyr Ser Ser<br>                    325                      330                      335 | 1008 |
| gtt ggg tat tct ctg ctt ctc aag aag gag aag gca atc atc gtt cag<br>Val Gly Tyr Ser Leu Leu Leu Lys Lys Glu Lys Ala Ile Ile Val Gln<br>                    340                      345                      350 | 1056 |
| cct gat cgg gtt act atc ggt aac gga cct gcg ttt gga tgt gtt ctt<br>Pro Asp Arg Val Thr Ile Gly Asn Gly Pro Ala Phe Gly Cys Val Leu<br>                    355                      360                      365 | 1104 |
| atg aag gat ttt cta agc gag ttg gct aaa cga att aag cac aac aac<br>Met Lys Asp Phe Leu Ser Glu Leu Ala Lys Arg Ile Lys His Asn Asn<br>370                      375                      380 | 1152 |
| act tct tat gag aat tat cac agg atc tat gtc cca gaa gga aag cct<br>Thr Ser Tyr Glu Asn Tyr His Arg Ile Tyr Val Pro Glu Gly Lys Pro<br>385                      390                      395                      400 | 1200 |
| ttg aga gat aac ccg aat gag tct ttg agg gtt aat gta ctg ttc caa<br>Leu Arg Asp Asn Pro Asn Glu Ser Leu Arg Val Asn Val Leu Phe Gln<br>                    405                      410                      415 | 1248 |
| cac att cag aat atg ctc tct tct gag tct gct gtg ctt gct gag aca<br>His Ile Gln Asn Met Leu Ser Ser Glu Ser Ala Val Leu Ala Glu Thr<br>                    420                      425                      430 | 1296 |
| gga gat tcc tgg ttc aac tgt cag aag ctg aag ctc cct gaa gga tgc<br>Gly Asp Ser Trp Phe Asn Cys Gln Lys Leu Lys Leu Pro Glu Gly Cys<br>                    435                      440                      445 | 1344 |
| ggt tac gaa ttc caa atg cag tac gga tca att ggc tgg tca gtg ggt<br>Gly Tyr Glu Phe Gln Met Gln Tyr Gly Ser Ile Gly Trp Ser Val Gly<br>                    450                      455                      460 | 1392 |
| gct act cta ggc tat gct caa gcc atg cca aac agg cgt gtc att gct<br>Ala Thr Leu Gly Tyr Ala Gln Ala Met Pro Asn Arg Arg Val Ile Ala<br>465                      470                      475                      480 | 1440 |
| tgt att gga gat ggt agt ttc cag gta acc gca cag gat gta tct acg<br>Cys Ile Gly Asp Gly Ser Phe Gln Val Thr Ala Gln Asp Val Ser Thr<br>                    485                      490                      495 | 1488 |
| atg ata cgg tgt ggg caa aag acc ata atc ttc ctc atc aac aac gga<br>Met Ile Arg Cys Gly Gln Lys Thr Ile Ile Phe Leu Ile Asn Asn Gly<br>                    500                      505                      510 | 1536 |

-continued

```
ggc tac acc att caa gtg gaa att cac gat ggt cct tac aat gtc ata      1584
Gly Tyr Thr Ile Gln Val Glu Ile His Asp Gly Pro Tyr Asn Val Ile
        515                 520                 525 aag aac tgg aac tac aca gct ttt gtt gag gcc ata cac aat gga gaa      1632
Lys Asn Trp Asn Tyr Thr Ala Phe Val Glu Ala Ile His Asn Gly Glu
    530                 535                 540 gga aaa tgc tgg act gcc aag gtg aga tgc gag gag gag tta gtg aaa      1680
Gly Lys Cys Trp Thr Ala Lys Val Arg Cys Glu Glu Glu Leu Val Lys
545                 550                 555                 560 gca atc aac acg gca acc aat gag gaa aaa gag agc ttt tgt ttc att      1728
Ala Ile Asn Thr Ala Thr Asn Glu Glu Lys Glu Ser Phe Cys Phe Ile
                565                 570                 575 gaa gtg ata gtg cac aaa gac gat aca agc aag gaa ctt ttg gag tgg      1776
Glu Val Ile Val His Lys Asp Asp Thr Ser Lys Glu Leu Leu Glu Trp
            580                 585                 590 ggc tct aga gtc tct gct gct aat agt cgt ccc cca aat ccg cag tag      1824
Gly Ser Arg Val Ser Ala Ala Asn Ser Arg Pro Pro Asn Pro Gln
        595                 600                 605
```

<210> SEQ ID NO 8
<211> LENGTH: 607
<212> TYPE: PRT
<213> ORGANISM: Arabidopsis thaliana

<400> SEQUENCE: 8

```
Met Asp Thr Lys Ile Gly Ser Ile Asp Ala Cys Asn Pro Thr Asn His
1               5                   10                  15

Asp Ile Gly Gly Pro Asn Gly Val Ser Thr Val Gln Asn Thr
                20                  25                  30

Ser Pro Leu His Ser Thr Val Ser Pro Cys Asp Ala Thr Leu Gly
            35                  40                  45

Arg Tyr Leu Ala Arg Arg Leu Val Glu Ile Gly Val Thr Asp Val Phe
        50                  55                  60

Ser Val Pro Gly Asp Phe Asn Leu Thr Leu Leu Asp His Leu Ile Ala
65                  70                  75                  80

Glu Pro Asn Leu Lys Leu Ile Gly Cys Cys Asn Glu Leu Asn Ala Gly
                85                  90                  95

Tyr Ala Ala Asp Gly Tyr Ala Arg Ser Arg Gly Val Gly Ala Cys Val
            100                 105                 110

Val Thr Phe Thr Val Gly Gly Leu Ser Val Leu Asn Ala Ile Ala Gly
        115                 120                 125

Ala Tyr Ser Glu Asn Leu Pro Leu Ile Cys Ile Val Gly Gly Pro Asn
    130                 135                 140

Ser Asn Asp Tyr Gly Thr Asn Arg Ile Leu His His Thr Ile Gly Leu
145                 150                 155                 160

Pro Asp Phe Thr Gln Glu Leu Arg Cys Phe Gln Ala Val Thr Cys Phe
                165                 170                 175

Gln Ala Val Ile Asn Asn Leu Glu Glu Ala His Glu Leu Ile Asp Thr
            180                 185                 190

Ala Ile Ser Thr Ala Leu Lys Glu Ser Lys Pro Val Tyr Ile Ser Ile
        195                 200                 205

Ser Cys Asn Leu Pro Ala Ile Pro Leu Pro Thr Phe Ser Arg His Pro
    210                 215                 220

Val Pro Phe Met Leu Pro Met Lys Val Ser Asn Gln Ile Gly Leu Asp
225                 230                 235                 240

Ala Ala Val Glu Ala Ala Ala Glu Phe Leu Asn Lys Ala Val Lys Pro
```

```
                    245                 250                 255
Val Leu Val Gly Gly Pro Lys Met Arg Val Ala Lys Ala Ala Asp Ala
                260                 265                 270

Phe Val Glu Leu Ala Asp Ala Ser Gly Tyr Gly Leu Ala Val Met Pro
            275                 280                 285

Ser Ala Lys Gly Gln Val Pro Glu His His Lys His Phe Ile Gly Thr
        290                 295                 300

Tyr Trp Gly Ala Val Ser Thr Ala Phe Cys Ala Glu Ile Val Glu Ser
305                 310                 315                 320

Ala Asp Ala Tyr Leu Phe Ala Gly Pro Ile Phe Asn Asp Tyr Ser Ser
                325                 330                 335

Val Gly Tyr Ser Leu Leu Leu Lys Lys Glu Lys Ala Ile Ile Val Gln
            340                 345                 350

Pro Asp Arg Val Thr Ile Gly Asn Gly Pro Ala Phe Gly Cys Val Leu
        355                 360                 365

Met Lys Asp Phe Leu Ser Glu Leu Ala Lys Arg Ile Lys His Asn Asn
    370                 375                 380

Thr Ser Tyr Glu Asn Tyr His Arg Ile Tyr Val Pro Glu Gly Lys Pro
385                 390                 395                 400

Leu Arg Asp Asn Pro Asn Glu Ser Leu Arg Val Asn Val Leu Phe Gln
                405                 410                 415

His Ile Gln Asn Met Leu Ser Ser Glu Ser Ala Val Leu Ala Glu Thr
            420                 425                 430

Gly Asp Ser Trp Phe Asn Cys Gln Lys Leu Lys Leu Pro Glu Gly Cys
        435                 440                 445

Gly Tyr Glu Phe Gln Met Gln Tyr Gly Ser Ile Gly Trp Ser Val Gly
    450                 455                 460

Ala Thr Leu Gly Tyr Ala Gln Ala Met Pro Asn Arg Arg Val Ile Ala
465                 470                 475                 480

Cys Ile Gly Asp Gly Ser Phe Gln Val Thr Ala Gln Asp Val Ser Thr
                485                 490                 495

Met Ile Arg Cys Gly Gln Lys Thr Ile Ile Phe Leu Ile Asn Asn Gly
            500                 505                 510

Gly Tyr Thr Ile Gln Val Glu Ile His Asp Gly Pro Tyr Asn Val Ile
        515                 520                 525

Lys Asn Trp Asn Tyr Thr Ala Phe Val Glu Ala Ile His Asn Gly Glu
    530                 535                 540

Gly Lys Cys Trp Thr Ala Lys Val Arg Cys Glu Glu Glu Leu Val Lys
545                 550                 555                 560

Ala Ile Asn Thr Ala Thr Asn Glu Glu Lys Glu Ser Phe Cys Phe Ile
                565                 570                 575

Glu Val Ile Val His Lys Asp Asp Thr Ser Lys Glu Leu Leu Glu Trp
            580                 585                 590

Gly Ser Arg Val Ser Ala Ala Asn Ser Arg Pro Pro Asn Pro Gln
        595                 600                 605

<210> SEQ ID NO 9
<211> LENGTH: 27
<212> TYPE: DNA
<213> ORGANISM: Artificial
<220> FEATURE:
<223> OTHER INFORMATION: Oligonucleotide useful as a primer

<400> SEQUENCE: 9
ccgacgaaaa cggcaagaaa aagcagt                                          27
```

<210> SEQ ID NO 10
<211> LENGTH: 24
<212> TYPE: DNA
<213> ORGANISM: Artificial
<220> FEATURE:
<223> OTHER INFORMATION: Oligonucleotide useful as a primer

<400> SEQUENCE: 10
ccagaagttc tttttccagt acct                                    24

<210> SEQ ID NO 11
<211> LENGTH: 20
<212> TYPE: DNA
<213> ORGANISM: Artificial
<220> FEATURE:
<223> OTHER INFORMATION: Oligonucleotide useful as a primer

<400> SEQUENCE: 11
tttcttgccg ttttcgtcgg                                         20

<210> SEQ ID NO 12
<211> LENGTH: 20
<212> TYPE: DNA
<213> ORGANISM: Artificial
<220> FEATURE:
<223> OTHER INFORMATION: Oligonucleotide useful as a primer

<400> SEQUENCE: 12
actggaaaaa gaacttctgg                                         20

<210> SEQ ID NO 13
<211> LENGTH: 21
<212> TYPE: DNA
<213> ORGANISM: Artificial
<220> FEATURE:
<223> OTHER INFORMATION: Oligonucleotide useful as a primer

<400> SEQUENCE: 13
tgatagtgat agtgatagtg a                                       21

<210> SEQ ID NO 14
<211> LENGTH: 21
<212> TYPE: DNA
<213> ORGANISM: Artificial
<220> FEATURE:
<223> OTHER INFORMATION: Oligonucleotide useful as a primer

<400> SEQUENCE: 14
agcgttagcg ttagcgttag c                                       21

<210> SEQ ID NO 15
<211> LENGTH: 44
<212> TYPE: DNA
<213> ORGANISM: Artificial
<220> FEATURE:
<223> OTHER INFORMATION: Oliigonucleotide useful as a primer

<400> SEQUENCE: 15
tttcttgccg ttttcgtcgg tatagattcg tacttgttaa aggt              44

<210> SEQ ID NO 16
<211> LENGTH: 60
<212> TYPE: DNA
<213> ORGANISM: Artificial
<220> FEATURE:

-continued

```
<223> OTHER INFORMATION: Oligonucleotide useful as a primer

<400> SEQUENCE: 16
tgatagtgat agtgatagtg agagctccca tgggaccggc atatatcaat gcatgctttt      60

<210> SEQ ID NO 17
<211> LENGTH: 45
<212> TYPE: DNA
<213> ORGANISM: Artificial
<220> FEATURE:
<223> OTHER INFORMATION: Oligonucleotide useful as a primer

<400> SEQUENCE: 17
actggaaaaa gaacttctgg ccttagattc gtacttgtta aaggt                      45

<210> SEQ ID NO 18
<211> LENGTH: 60
<212> TYPE: DNA
<213> ORGANISM: Artificial
<220> FEATURE:
<223> OTHER INFORMATION: Oligonucleotide useful as a primer

<400> SEQUENCE: 18
agcgttagcg ttagcgttag caagcttctg catgaccggc atatatcaat gcatgctttt      60

<210> SEQ ID NO 19
<211> LENGTH: 49
<212> TYPE: DNA
<213> ORGANISM: Artificial
<220> FEATURE:
<223> OTHER INFORMATION: Oligonucleotide useful as a primer

<400> SEQUENCE: 19
tttcttgccg ttttcgtcgg taagctcatc gagctaaaac ctactgtaa                  49

<210> SEQ ID NO 20
<211> LENGTH: 50
<212> TYPE: DNA
<213> ORGANISM: Artificial
<220> FEATURE:
<223> OTHER INFORMATION: Oligonucleotide useful as a primer

<400> SEQUENCE: 20
actggaaaaa gaacttctgg cctagctcat cgagctaaaa cctactgtaa                 50

<210> SEQ ID NO 21
<211> LENGTH: 59
<212> TYPE: DNA
<213> ORGANISM: Artificial
<220> FEATURE:
<223> OTHER INFORMATION: Oligonucleotide useful as a primer

<400> SEQUENCE: 21
tgatagtgat agtgatagtg atctagacca tggcaacctg gtcacattca cacgtttaa      59

<210> SEQ ID NO 22
<211> LENGTH: 53
<212> TYPE: DNA
<213> ORGANISM: Artificial
<220> FEATURE:
<223> OTHER INFORMATION: Oligonucleotide useful as a primer

<400> SEQUENCE: 22
agcgttagcg ttagcgttag cggatcccaa cctggtcaca ttcacacgtt taa             53
```

```
<210> SEQ ID NO 23
<211> LENGTH: 48
<212> TYPE: DNA
<213> ORGANISM: Artificial
<220> FEATURE:
<223> OTHER INFORMATION: OLigonucleotide useful as a primer

<400> SEQUENCE: 23
tagagtgagc tcccatggac actaagatcg gatctatcga cggctgta            48

<210> SEQ ID NO 24
<211> LENGTH: 54
<212> TYPE: DNA
<213> ORGANISM: Artificial
<220> FEATURE:
<223> OTHER INFORMATION: Oligonucleotide useful as a primer

<400> SEQUENCE: 24
attgtaagga ccatcgtgaa tttccacctg aatggtgtag cctccgttgt tgat      54

<210> SEQ ID NO 25
<211> LENGTH: 54
<212> TYPE: DNA
<213> ORGANISM: Artificial
<220> FEATURE:
<223> OTHER INFORMATION: Oligonucleotide useful as a primer

<400> SEQUENCE: 25
atcaacaacg gaggctacac cattcaggtg gaaattcacg atggtcctta caat      54

<210> SEQ ID NO 26
<211> LENGTH: 48
<212> TYPE: DNA
<213> ORGANISM: Artificial
<220> FEATURE:
<223> OTHER INFORMATION: Oligonucleotide useful as a primer

<400> SEQUENCE: 26
ttcgatggat ccctactgcg gatttggggg acgactatta gcagcaga            48
```

CONDITIONAL STERILITY IN PLANTS

CROSS-REFERENCE TO RELATED APPLICATIONS

This application is the National Stage of International Application No. PCT/US 2004/018058, filed Jun. 3, 2004, which application claims benefit of U.S. Provisional Application 60/475,551, filed Jun. 3, 2003.

ACKNOWLEDGEMENT OF FEDERAL RESEARCH SUPPORT

This invention was made with funding under Grant No. DEFG796ER2027 from the Department of Energy and Contract No. R01 GM36397-14A1 from the National Institutes of Health. The government has certain rights in this invention.

BACKGROUND OF THE INVENTION

The field of the present invention is plant molecular biology, especially as related to genetically modified plants with conditional male sterility. Specifically, the present invention relates to conditionally male and/or female sterile plants in which sterility is achieved by disrupting the availability of thiamine by high affinity binding proteins expressed in pollen and/or in the developing ovule, by inhibiting functional expression of one or more thiamine biosynthetic proteins or by destroying thiamine in those plant tissues.

Systems of plant sterility are essential tools in the hybrid seed industry, forestry, conservation biology, and phytoremediation. The hybrid seed industry plants millions of acres of in which one of the two elite parent plants in a genetic cross is male sterile as a result of physical or genetic emasculation. Male sterility is the basis for this 400 million dollar per year industry. Foresters are interested in plant sterility, because wood production is dramatically reduced when nitrogen and phosphorus are drained into pollen and megagametophyte production. In addition, genetically engineered trees, shrubs, and grasses are being developed that extract, detoxify, and/or sequester toxic pollutants and for phytomining of precious elements. Conditional male sterility adds value to and limits unauthorized propagation of valuable plants for any purpose. Plant sterility systems are needed if genetically modified organisms (GMOs) are to be released into the natural environment with no release of their germplasm. In this case, complete male-female sterility is desirable so that the organisms cannot reproduce seed by any means.

Numerous strategies have been used to generate male sterility for the hybrid seed industry ranging from manually emasculating plants, altering the levels of essential metabolites in pollen, and generating toxins in developing pollen with two component systems (Perez-Prat and van Lookeren Campagne, 2002). Another approach has been to make the essential vitamin cofactor biotin unavailable in reproductive tissues to render a plant sterile. Applying this harmless vitamin to the plants then restores fertility (Albertsen and Howard, 1999).

There is a need in the art for economical and safe compositions and methods for rendering plants male and/or female sterile, especially where the sterility can be controlled so as to allow the production of viable seeds under controlled conditions.

SUMMARY OF THE INVENTION

The present invention provides DNA constructs comprising tissue specific transcription regulatory sequences which direct expression of an associated sequence in developing pollen and/or ovules and operably linked to the transcription regulatory sequence, a sequence which when expressed, ablates the availability of thiamine in developing pollen or ovules, either by expression of at least one interfering RNA or antisense RNA specific to at least one thiamine biosynthetic enzyme (e.g., AtThi2 or AtThi3) or by the expression of a high affinity thiamine binding protein (e.g., an enzymatically inactive PDC2) such that thiamine is sequestered in the developing pollen and/or ovules or by expression of a thiamine-degrading enzyme (thiaminase). Also within the scope of the present invention are vectors and recombinant host cells comprising the DNA constructs of the present invention. Pollen-specific or pollen- and ovule-specific transcription regulatory sequences, as specifically exemplified herein, include the transcriptional regulatory sequences of the *Arabidopsis thaliana* Act11, Act12, or Act2 or Lat52p genes. The target for inhibiting expression of a thiamine biosynthetic gene can be AtThi2 or AtThi3. The AtPDC gene can be modified to produce a thiamine-sequestering protein in pollen and/or ovules as described herein. As specifically exemplified, the thiamine-sequestering derivative has coding and amino acid sequences as given in SEQ ID No: 7-8. The sterility resulting from the regulated expression of the constructs of the present invention is conditional; fertility is restored by the application of thiamine to the flowers, for example, in a spray which may optionally further comprise a surfactant such as 0.1% Silwet or Triton X100 (allyloxypolyethyleneglycol methyl ether, OSi Specialties, Inc, Tarrytown, N.Y. or t-octylphenoxypolyethoxyethanol) or in the growth medium.

There are numerous hydroxyethylthiazole kinase (HTK) and phosphomethylpyrimidine kinase (PPK) sequences available on the internet site for The National Center for Biotechnology Information, including the following accession numbers: CA765813, U38199, U27350, *Oryza sativa*; BU964708, BM524834, BG725189, *Glycine max*, CA900839, CA900838, CA896676, CA896675, *Phaseolus coccineus*; AF193791, *Fragaria x ananassa*; AJ251246, *Saccharum officinarum*; X81855, *Nicotiana tabacum*; BM 177583, *Glycine max*; and BQ618938, *Zea mays*.

Thiaminase can be expressed under the regulatory control of pollen-specific or pollen- and ovule-specific promoter sequences, with the result that thiamine in the relevant reproductive tissue is degraded and that tissue cannot develop for its intended function.

For the RNAi strategy for conditional plant sterility, it is preferred that there be a very high degree (greater than 95%) of sequence identity between the expressed RNAi nucleotide sequence and the target gene. Preferably, the RNAi construct is derived in sequence from the same plant source and is identical in sequence to the target sequence.

While the AtACT11 and AtACT12 promoters (transcription regulatory sequences) are specifically exemplified herein, the skilled artisan can isolate the corresponding tissue specific promoters from other species and use them in the conditional plant sterility methods of the present invention as well.

The present invention further provides recombinant plant cells, recombinant plant tissue and transgenic plants which contain the DNA constructs of the present invention. Transgenic plants which contain the DNA construct are conditionally male sterile or male-female sterile, i.e.; they are sterile in the absence of exogenously supplied thiamine.

Also within the scope of the present invention are methods for rendering a plant of interest conditionally male and/or female sterile. The method comprises the steps of introducing a vector comprising a DNA construct containing a pollen-specific or pollen- and/or ovule-specific transcriptional regulatory sequence operably linked to a sequence which, when expressed, renders the developing pollen and/or ovules deficient in thiamine. This can be achieved by expression in the developing the pollen and/or ovules of a thiaminase or a protein in the developing pollen which binds thiamine with high affinity or it can be achieved by the expression in developing pollen of an antisense RNA or an interference RNA specific to a sequence which specifies a thiamine biosynthetic enzyme. Supplementation of the transgenic plant during flowering with exogenous thiamine temporarily restores sterility. The methods of the present invention are applicable in forestry, horticulture, agriculture, conservation and phytoremediation, among other areas.

BRIEF DESCRIPTION OF THE DRAWINGS

FIGS. 4A-4C provide the *Arabidopsis thaliana* bifunctional phosphomethylpyrimidine kinase/thiamine phosphate pyrophosphorylase (PPK/TPP) (AtThi2) nucleotide and amino acid sequences, SEQ ID NO:1 and SEQ ID NO:2, respectively.

FIGS. 5A-5B provide the *Arabidopsis thaliana* hydroxyethylthiazole kinase (HTK) (AtThi3) nucleotide and amino acid sequences, SEQ ID NO:3 and SEQ ID NO:4, respectively.

FIGS. 6A-6B provide the *Arabidopsis thaliana* pyruvate decarboxylase (AtPDC2) nucleotide and amino acid sequences, SEQ ID NO:5 and 6, respectively. A mutation ($PDC_{E517Q}$) useful in the present conditional plant sterility strategy is indicated; the enzymatically inactive, thiamine-binding mutant coding and amino acid sequences are given in SEQ ID NO:7 and SEQ ID NO:8, respectively.

FIG. 8 provides a restriction map of AtThi2. Restriction endonucleases which do not cleave in this region include ApaI, BglII, EcoRI, KpnI, NotI, SacII, SalI, SmaI, SpeI and XhoI. Primer sets useful for PCR manipulations of this gene are also shown.

FIG. 9 provides a restriction map of the AtThi3 gene. Restriction endonucleases which do not cleave in this region include ApaI, BglII, EcoRI, HindIII, KpnI, NotI, PstI, SacI, SacII, SalI, SmaI, SpeI and XhoI. Primer sets useful for PCR manipulations of this gene are also shown.

FIG. 10 provides a restriction map of the AtPDC gene. Restriction endonucleases which do not cleave in this region include BamHI, HindIII, NcoI, NotI, PstI, SacI, SalI, SmaI, SpeI, and XhoI. Primer sets useful for PCR manipulation of this region are also shown.

DETAILED DESCRIPTION OF THE INVENTION

Figure 1:
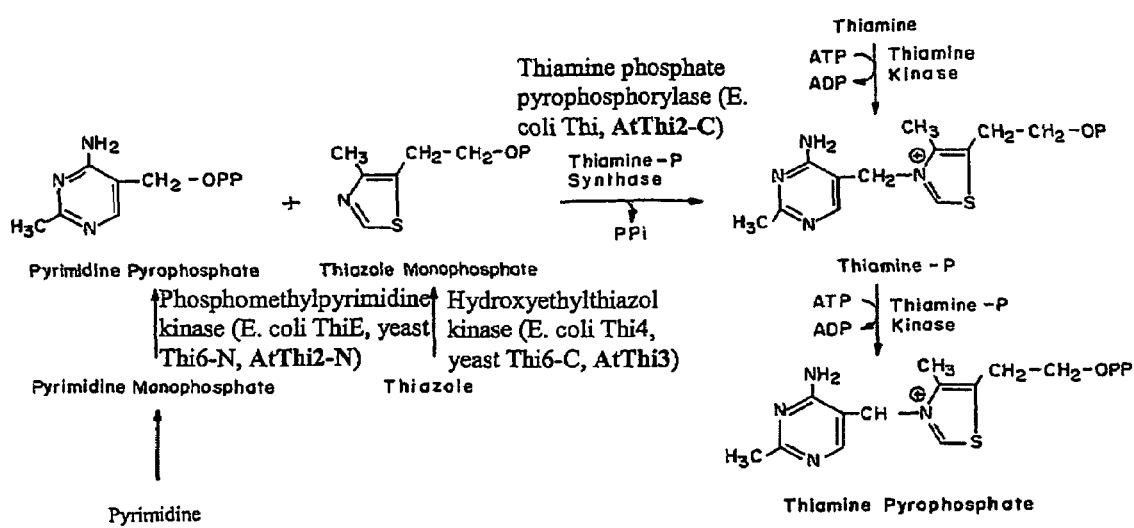
FIG. 1 illustrates the thiamine biosynthetic pathway.

As used herein, a male sterile is a plant which does not produce pollen. Seed sterility is where viable seeds are not produced to embryo lethality. Female sterility refers to the inability of the female germline of a plant (ovule and endosperm) to develop, receive pollen or develop once fertilized, and there is no introgression, selfing or outcrossing. Where there is female sterility, pollen from a native plant cannot fertilize the engineered female sterile plant and no fertile offspring are produced.

Systems of plant sterility are important tools in the hybrid seed industry, forestry, and phytoremediation. The hybrid seed industry, for example, plants millions of acres in which one of the two elite parent plants in a genetic cross is male sterile as a result of physical or genetic emasculation. In phytoremediation, genetically engineered plants are being developed that extract, detoxify, and/or sequester toxic pollutants, and their germplasm needs to be tightly controlled. In this case, systems of male and female sterility are needed if plants are to be released permanently into the environment. Control of fertility also limits unauthorized propagation of proprietary material. An especially useful sterility system is one in which sterility is conditional, and in which elite parental lines can still be propagated through fully fertile crosses. The present invention provides a conditional sterility system based on suppression of the pathway for thiamine B1 synthesis, sequestration of thiamine or destruction of thiamine B1 during pollen and/or ovule development such that the plants exhibit thiamine-deficiency based conditional sterility (TDCS). Fertility of the TDCS plants is restored by treatment with excess thiamine, a harmless vitamin. In addition, plant sterility can improve the economics of wood and pulpwood production because phosphorus and nitrogen are not "wasted" in the production of pollen and seed. This is particularly applicable to pine and eucalyptus. Controlled sterility is also applicable to genetically modified turfgrass or bentgrass; to the production of seedless fruit such as watermelon or grapes. These methods can also be applied to the animal forage crops; many forage crops such as alfalfa, fescue and Bermuda grass decline in feed quality when they go to seed. Similarly, the sugar yield from sugar cane is improved if the cane does not go to seed as a result of genetic modification to contain and express a conditional sterility construct of the present invention. A particularly important advantage of the present invention is that it is not labor-intensive.

TDCS can be achieved by altering the expression of three different genes in the model plant *Arabidopsis*. Two genes, AtThi2 and AtThi3, encoding a bifunctional enzyme (phosphomethylpyrimidine kinase, thiamine phosphate pyrophosphorylase also called thiamine synthase) and a monofunctional enzyme (hydroxyethylthiazole kinase) in the thiamine B1 synthesis pathway, respectively, are targeted for suppression in *Arabidopsis* reproductive tissue. RNA interference (RNAi) is used to degrade target AtThi2 and AtThi3 RNAs using three distinct actin promoter vector systems: ACT12pt directs pollen specific suppression; ACT11pt directs pollen/ovule specific suppression; and ACT2pt serves as a control by suppressing these genes in all vegetative tissues. In addition, TDCS can be achieved by sequestering thiamine in reproductive tissues by the overexpressing a mutant form of *Arabidopsis* pyruvate decarboxylase (PDC). Alternatively, or in addition, a thiaminase coding sequence can be expressed under the regulatory control of tissue specific promoters as described therein. The resulting plants with one or more of these transgenes are sterile under normal soil growth conditions, but fully fertile when supplemented with excess thiamine B1.

Thiamine (Vitamin B1) is an essential vitamin in mammals. Plants make their own thiamine, because it is an essential cofactor in metabolism. For example, pyruvate decarboxylase, xylulose transketolase, and acetolactate synthase (Chang and Duggleby, 1997), and other enzymes that convert carboxyl groups to aldehydes or ketones, require thiamine B1 (Bouvier et al., 1998). Thiamine biosynthesis can be ablated or thiamine can be sequestered in reproductive organs and tissues to create conditional auxotrophic sterile mutants ("knockdown lines") that require thiamine for fertility.

Arabidopsis thiamine (B1) auxotrophic mutants grow well with exogenously added B1 in their growth medium (Li and Redei, 1969; Redei and Li, 1969; Ledoux et al., 1974). Plants appear to use a thiamine (B1) biosynthesis pathway similar to that described in bacteria and yeast, the final steps of which are shown in FIG. 1 (Brown and Williamson, 1987). Pyrimidine pyrophosphate and thiazole monophosphate are combined by the action of thiamine phosphate synthase to make thiamine phosphate. The pyrimidine and thiazole derived components are both made by poorly characterized biochemical pathways (Brown and Williamson, 1987). In the last decade several genes encoding enzymes or regulatory proteins in the thiamine pathway have been characterized in Escherichia coli, Saccharomyces cerevisiae and Schizosaccharomyces pombe.

We have identified genes involved in thiamine B1 synthesis in the Arabidopsis database. Using yeast, S. pombe, and E. coli query sequences, we found several genes encoding homologues to B1 synthesis enzymes. No attempt was made to identify DNA regulatory proteins involved in thiamine synthesis. Examples of the relevant Arabidopsis sequences identified with potential roles in thiamine synthesis or binding are listed in Table 1. This analysis reveals several gene sequence targets in the Arabidopsis genome that are believed essential for thiamine B1 biosynthesis, modification, and degradation. Many of them are single-copy or low-copy genes, which simplifies any strategy for blocking thiamine synthesis or sequestering available thiamine in plant cells.

Only one Arabidopsis gene (AtThi1) implicated in thiamine B1 synthesis (AtThi1) has been partially characterized for function (Machado et al., 1996; Machado et al., 1997; Chabregas et al., 2001). This gene complements E. coli mutations that affect DNA repair, such as uvrA. AtThi1 is also a sequence homologue of the B1 biosynthetic genes of yeast Thi4 and S. pombe Thi2. AtThi1 complements yeast mutants in the essential Thi4 gene (FIGS. 1 and 2), and it appears to complement both yeast cell viability and DNA repair activity as measured for mitochondrial DNA. Using either S. pombe Thi2 or yeast Thi4 protein as the query sequence, we detected a single Arabidopsis Thi1 sequence (NP200288). It has very strong homology over most of its length and 65% identity to the S. pombe Thi2 (Nmt2) protein (Table I, AtThi1). Thus, AtThi1 appears to be a single copy gene. AtThi1 is synthesized in the cytoplasm and then transported into to both the chloroplast and mitochondria by means of a dual N-terminal peptide targeting sequence (Chabregas et al., 2001). Because of this and other information on protein localization of other enzymes in thiamine synthesis, it appears that plant nuclear genes encode thiamine B1 synthesis enzymes. The transcripts are translated on cytoplasmic ribosomes, but thiamine B1 synthesis itself takes place primarily in organellar compartments. AtThi1 is only a secondary target for functional inactivation, because its complex biochemical activities are still poorly defined.

AtThi2 and AtThi3: Yeast Thi6 is a 540 amino acid bifunctional enzyme acting as both a phosphomethylpyrimidine kinase and a hydroxyethylthiazole kinase (FIG. 1). Its N-terminal half is homologous to E. coli ThiE, phosphomethylpyrimidine kinase (Table 1). The C-terminal half of yeast Thi6 is homologous to E. coli Thi4, a hydroxyethylthiazole kinase. Using the yeast Thi6 sequence as a query, we detected two proteins in Arabidopsis, NP_172707 and NP_189045, and found homology to the N-terminal and C-terminal halves of the Thi6 query (see Table 1), respectively. We have named these sequences AtThi2 and AtThi3, respectively. AtThi2 and AtThi3 are very different in length (525 and 276 amino acids) and are not homologous to each other. AtThi2 is about the same length as yeast Thi6, but only has homology in its N-terminal half. The question thus becomes, what does the C-terminal half of AtThi2 encode? Using the C-terminal 250 amino acids of AtThi2 as a query against all sequences, we found a thiamine phosphate pyrophosphorylase sequence (thiE, NP_579063) from Pyrococcus furiosus as the most homologous of many non-plant sequences that are significantly related to this Arabidopsis query (E-value=e-35). In addition, using the yeast thiamine phosphate pyrophosphorylase Thi22 (Goffeau et al., 1996), we found a single Arabidopsis homologue, and it was again the C-terminal, 250 amino acid end of AtThi2 (NP_173707, Table 1, and see below). Without wishing to be bound by any particular theory, we have concluded that AtThi2 is a different bifunctional enzyme than yeast Thi6. AtThi2 combines an N-terminal phosphomethylpyrimidine kinase with a C-terminal thiamine phosphate pyrophosphorylase (thiamine synthase) (FIG. 1). Similarly, and again without wishing to be bound by theory, we have concluded that AtThi3 is a mono-functional hydroxyethylthiazole kinase, corresponding to the C-terminal portion of the bifunctional yeast Thi6 (FIG. 1).

TABLE 1

Arabidopsis sequence targets to block thiamine B1 biosynthesis

| Thi sequence query[a]/ Organism | Ath homolog[b] Accession # Length a.a. | (# seq.) E value | % ID | Length hom. a.a./query | Comments/Reference |
|---|---|---|---|---|---|
| Thi2 (nmt2) NP_596642 S. pombe | NP_200288 349 a.a. AtThi1 | (1)3e−93 | 65% | 266/328 | (Manetti et al., 1994) Thi1 Ath (Machado et al., 1996; Machado et al., 1997; Chabregas et al., 2001) |
| Thi4 S25321 NP_011660 yeast | ARA6, Thi1, NP_200288 349 a.a. | 3e−77 | 50%- | 310-100/326 | thiamin biosynthesis protein thi4, thiozole biosyn. |
| Thi2p NP_009799 yeast | No sig. homologue | >0.2 | | 450 | Ts activator of Thi B1 genes |

TABLE 1-continued

Arabidopsis sequence targets to block thiamine B1 biosynthesis

| Thi sequence query[a]/ Organism | Ath homolog[b] Accession # Length a.a. | (# seq.) E value | % ID | Length hom. a.a./query | Comments/Reference |
|---|---|---|---|---|---|
| Thi6 NP_015110 N-terminal domain | NP_173707 525 a.a. AtThi2 C-terminus | (1)7e−28 | 37% | 225/540 | Phosphomethypyrimidine kinase. Homology to a.a. 9-233 of query |
| C-terminal domain yeast | NP_189045 276 a.a. AtThi3 | (1)2e−20 | 30% | 240/540 | hydroxyethylthiazole kinase, putative, Homology to a.a. 255-523 of query |
| ThiE NP_312943 E. coli | NP_173707 525 a.a. AtThi2 C-term | 2e−11 | 33% | 185/211 | Phosphomethypyrimidine kinase |
| Thi4 NP_416607 E. coli | NP_189045 276 a.a. AtThi3 | 9e−43 | 42% | 240/262 | hydroxyethylthiazole kinase |
| Thi22, NP_015446 yeast. (S. pombe Pho4) | NP_173707 525 a.a. AtThi2 N-terminus | (1) e−35 | 33% | 274/572 C-term | See AtThi2 above, Also Brassica BTH1 thiamine phosphate pyrophosphorylase |
| THI80 P35202 yeast | NP_563669 264 a.a. AtThi5 | (4) 2e−17: 4e−8 | 26% | 270/319 a.a. | Thiamine pyrophosphokinase (TPK) Thiamine kinase, unknown |
| Thi3 BAA04886 & Thi3p NP_010203 yeast | B1 binding motif | (12) 3e−65: 5e−9 | 29-22% | (8) 550/568 & 609 | Yeast: Thiamine positive regulatory factor, Thiamine binding motif. Arabidopsis pyruvate decarboxylase (Nishimura et al., 1992) |
| Pyruvate decarboxylase PO6169 yeast | NP_195752 | (12) 4e−78: 7e−7 | 33%-31% | 560/563 | Pyruvate decarboxylase, oxal-CoA decarboxylase |

[a]Protein sequence from E. coli, S. cerevisiae, or S. pombe used as a query of the Arabidopsis genomic sequences.
[b]Predicted Arabidopsis protein sequence with homology detected in gDNA database (Arabidopsis Genome Initiative, 2000). For the purpose of clarity in identification of the Arabidopsis sequences, we will use Ath as a precursor to all Arabidopsis gene names.
[c]Number of predicted and distinct protein sequences with clear homology (N) followed by the range in E-values.

AtThi5: Thiamine pyrophosphate kinase (TPK, thiamine kinase) makes the pyrophosphate modified form of thiamine B1, shown at the bottom right of FIG. 1. Using the yeast gene THI80 (TPK) as a query, four Arabidopsis sequences with significant sequence homology were detected (Table 1). All four sequences may encode nearly identical proteins with truncations at the N-terminus. These proteins are believed to represent the products of a single gene, that we call AtThi5, with multiple allelic cDNAs. We have not yet confirmed whether all four sequences are in the same chromosomal location (same gene) or if they have significant silent nucleotide substitution differences and represent different genes. Yeast thi80 mutants have less thiamine, but are viable (Nishimura et al., 1991; Nosaka et al., 1993). However, because Thi80 is not an essential gene in yeast, the Arabidopsis homologue(s) has not been chosen as a target for functional inactivation.

AtPDC2: There are alternative or supplementary methods of creating TDCS in addition to blocking the synthesis of thiamine biosynthetic enzymes. Thiamine B1 can be sequestered in reproductive tissue, similar to the strategy using avidin to sequester biotin and thus create biotin-deficiency based male sterility (Albertsen and Howard, 1999). Although there is no precedent for generating sufficient thiamine sequestration capacity with a binding protein to create a deficiency, this concept is straightforward, as described herein. There is a thiamine binding protein activity found in plant seeds (Watanabe et al., 1998; Rapala-Kozik et al., 1999), but the genes and proteins for this activity are not identified. The well-characterized enzyme pyruvate decarboxylase (PDC) contains a strong thiamine B1 binding site. Three-dimensional models are available for PDCs from bacteria, fungi, and plants (Konig et al., 1998; Lu et al., 2000). PDC binds its thiamine B1 cofactor at the interface between two homodimeric subunits. Thiamine binding and subunit assembly appear to require the substrate pyruvate or an analogue. However, we believe that expression of large amounts of active PDC enzyme damages the efficiency of central metabolism. Thus, expression of an altered form of PDC that binds thiamine, but is enzymatically inactive, in plant reproductive tissue results in a sterile phenotype. The thiamine binding site is immediately adjacent to the pyruvate binding site. Mutant analysis of the bacterial enzyme from Zymomonas mobilis has yielded relevant and exciting results. Chang et al., 1999 have characterized several mutant active site mutant enzymes with a lower $K_m$ for substrate, most of which exhibit a lower affinity for thiamine. One PDC2 mutant with a single E473Q amino acid change lowers the specific activity to 0.025% of wild-type PDC levels (i.e., a 4000 fold reduction in activity), but appears to have an even tighter binding to thiamine than wild-type enzyme. Wild-type PDC has a $k_c$ for thiamine of 1.97 µM, while the release rate of thiamine from mutant enzyme $PDC_{E473Q}$ was too low to be measured. The affinity of $PDC_{E473Q}$ for thiamine could rival that of avidin for biotin. There is a strong sequence identity between the bacterial PDC and AtPDC2 in the region of bacterial residue $E_{473}$. Thus, we can engineer thiamine sequestration based on the tissue specific expression of a catalytically inactive, thiamine binding mutant AtPDC2 (E517Q) to achieve TDCS.

Thiamine sequestration based-sterility can stand alone or be used to supplement to genetic means for inactivating thiamine synthesis, for example, using interference RNA or antisense.

When a thiaminase coding sequence is operably linked to a pollen- and/or ovule-specific transcriptional regulatory sequence, the expressed thiaminase degrades thiamine in the relevant developing reproductive tissue. Thiaminase coding sequences are known to the art; see, e.g., Accession No. U17168 (*Paenibacillus/Bacillus thiaminolyticum* thiaminase) on the National Center for Biotechnology Information website. The skilled artisan can modify the codons for improved plant gene expression, if necessary. Murray et al. (1989) provides a discussion of codon choice in plants (Murray et al. (1989) *Nucl. Acids Res.* 17:477-494).

Thiaminases are also produced by other organisms including, but not limited to, *Clostridium sporogenes, Naegleria gruberi*, carp, lobsters, shrimp, certain clams and the fem bracken *Pteridium aquilinum* (See U.S. Patent Publication 2004/0013658 for a discussion).

Figure 2:
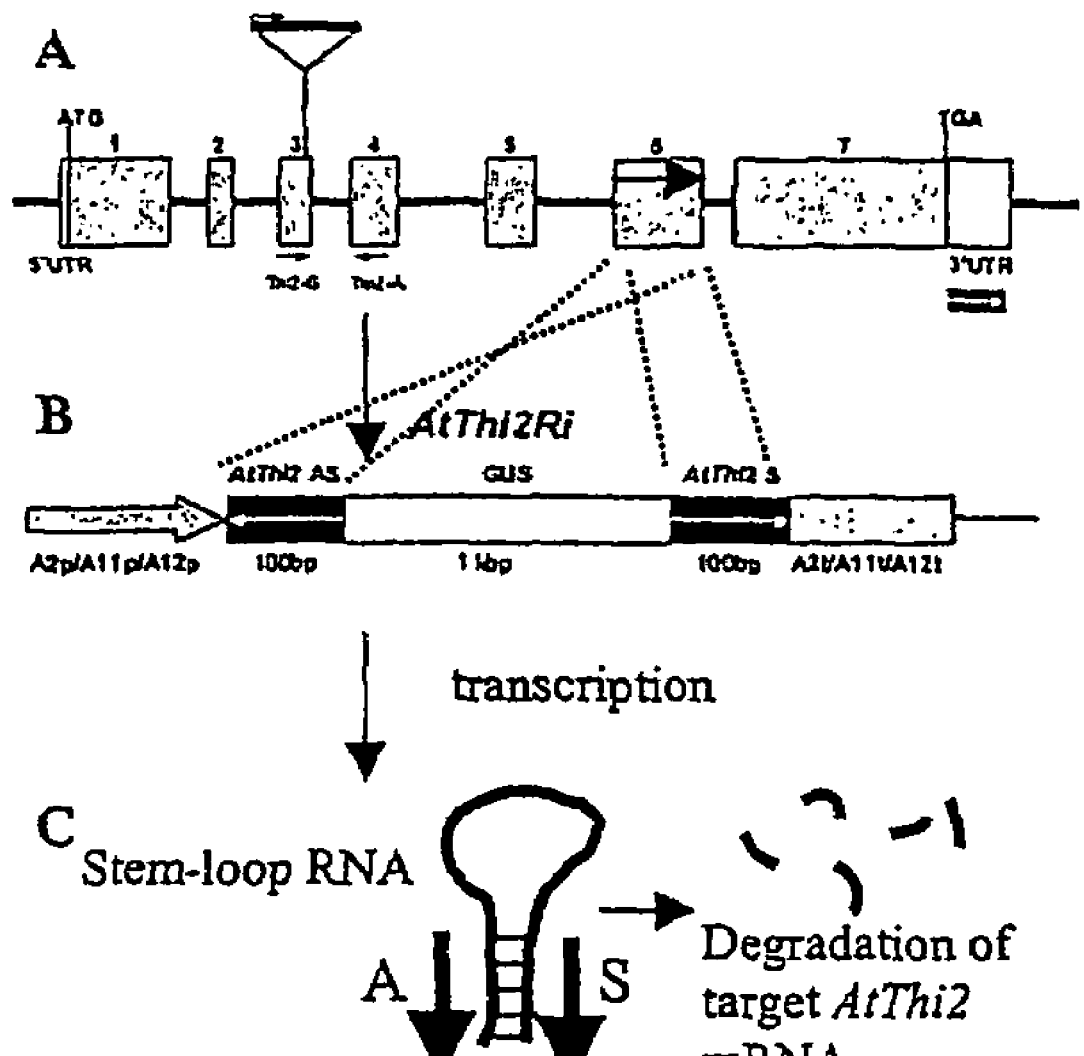
FIG. 2A illustrates the *Arabidopsis thaliana* AtThi2 gene structure with the thi2-1 mutant T-DNA insertion.
FIG. 2B illustrates expression (from A2pt:AtThi2Ri or A11pt:Thi2Ri or A12pt:Thi2Ri) of an antisense (A) oriented and sense (S) oriented 100 nucleotides of AtThi2 cDNA separated by a GUS spacer in a single transcript.
FIG. 2C shows that the RNA product of this engineered construct forms a stem-loop transcript that leads to degradation of native AtThi2 mRNA. (ts, transcriptional start; pA, polyadenylation sites).

Interference RNA (RNAi) can be used to suppress a gene activity by targeting an mRNA for efficient degradation (Chuang and Meyerowitz, 2000). A single RNA transcript is constructed so that the double stranded mRNA stem of its stem-loop structured RNA product is homologous to part of the target mRNA to be suppressed. This sets up a cycle of efficient target mRNA degradation. Our own laboratory has pioneered a technique to make RNAi constructs very rapidly (one day from PCR to cloning) using overlap extension PCR as described herein below. Using this technique, we have suppressed the levels of actin, profilin, and actin-related protein mRNAs and protein products. We have targeted 100 to 200 bp of the 3' untranslated regions (3'UTR) and/or 500 bp from the coding regions from these genes. 200 nt 3'UTR sequences from AtThi2 and AtThi3 were PCR amplified by this method to make an RNA product that folds into a stem-loop structure with a 200 bp dsRNA stem. An example of a construct expressing an RNAi to suppress AtThi2 expression is shown in FIG. 2. An inverted repeat-polymerase chain reaction (IR-PCR) technique is used to create the RNAi constructs in a short time. This technique circumvents the complex multistep cloning protocols generally needed to assemble RNAi constructs.

The ACT11pt vector is used to express an antisense (A) orientation and a sense (S) orientation from AtThi2 mRNA separated by a GUS spacer in a single transcript. The RNA product of this gene forms a stem-loop transcript that leads to the degradation of native AtThi2 mRNA. (ts, transcriptional start; pA, polyadenylation sites). The Act 11 promoter determines preferential expression of an associated sequence in pollen, ovules and in developing embryos, and it is also expressed in the leaves and stem of the inflorescence.

Pollen and ovule tissue-specific expression with the actin promoters: The tissue specific expression patterns of the specifically exemplified three promoter vectors is shown in Table 2 (for vector maps see FIGS. 3A-3C). The RNAi constructs are cloned into the ACT 11pt and ACT12pt vector derived from the *Arabidopsis* ACT11 and ACT12 actin gene promoters and pBI121, respectively (see FIGS. 3A, 3B). The homologous ACT11 and ACT12 terminators, respectively, have been added to update these promoter cassette vectors from their original versions (Huang et al., 1996; Huang et al., 1997). ACT11 is one of five reproductive actin genes. ACT11 is expressed very strongly in ovule, embryo, seed, silique, and pollen. We have already used ACT11pt-related constructs to inactivate ACT11 gene expression with an ACT11-RNAi construct. These ACT11/RNAi plants have a partially sterile phenotype. The use of the ACT11 promoter/terminator vector constructs was more successful at lowering ACT11 protein levels and producing phenotypes than were CaMV 35S promoted RNAi constructs. The ACT11-Thi2-RNAi or Thi3-RNAi constructs inactivate thiamine B1 biosynthesis in ovule, embryo, seed, silique, and pollen, producing a conditionally sterile phenotype.

TABLE 2

Vectors for reproductive and vegetative tissue-specific expression.

| Vector | Major tissue-specific expression | Origin |
|---|---|---|
| ACT11pt | Most reproductive tissues-embryo, ovule, seed, silique, mature pollen | *Arabidopsis* ACT11 actin gene |
| ACT12pt | Mature pollen | *Arabidopsis* ACT12 actin gene |
| ACT2pt | All vegetative tissues-leaves, roots, sepals, petals | *Arabidopsis* ACT2 actin gene |

ACT12 is the most tightly regulated of the *Arabidopsis* actin genes. It is expressed almost exclusively late in pollen development (Huang et al., 1996). Thi2- and Thi3-RNAi constructs expressed from the ACT12pt vector prevent the growth of mature pollen and block fertilization. Another suitable pollen-specific promoter is the Lat52p (Preuss et al., 1994). The constitutive ACT2 actin promoter cassette ACT2pt is used as a control to express the RNAi constructs in all vegetative tissues to make plants that do not grow at all without added thiamine.

The Thi-RNAi constructs are transformed or cotransformed into *Arabidopsis* via vacuum infiltration of each regulated RNAi construct subcloned into a *Agrobacterium* T-DNA plasmid (Bariola et al., 1999). Thi2-RNAi is subcloned into pCambia1300 with a hygromycin drug marker for plant selection (provided by Ray Wu, Cornell University, Ithaca, N.Y.). pCAMBIA 1300 and numerous other vectors for cloning and stable introduction of transgenes into plants are available from CAMBIA (Black Mountain, ACT, Australia). Where pBIN10 is used, selection is for kanamycin resistance. The Thi3-RNAi construct is subcloned into the pBIN19 vector with a kanamycin drug marker for plant selection (Bevan, 1984). With such transformations, progeny show between 0.1 and 2% of the seed to be transformed based on Hyg or Kan drug selection, and no non-transformed seeds escaped selection and grow. Plants doubly transformed with mixtures of *Agrobacterium* strains containing independent KanR and HygR plasmids are co-transformed at a rate of about 60%. When two different *Agrobacterium* populations carrying different T-DNAs are mixed and vacuum infiltrated together, their T-DNA transgenes are efficiently co-transformed into the same plants. Co-transformation saves three months over transforming the two genes in two successive separate rounds of transformation. The T1 generation of vacuum infiltrated transformed seed from the single and double Thi gene transformations are plated on media containing MS salts, the appropriate drugs for selection, and thiamine. Plants with one or both drug markers, expressing Thi2-RNAi, Thi3-RNAi or both Thi2-RNAi and Thi3-RNAi constructs, are characterized further for TDCS phenotypes.

The molecular model for Thi-RNAi suppression in these experiments is that the AtThi2 and AtThi3 mRNAs are degraded in reproductive tissues. RNA degradation results from the dsRNA structure of the transcript initiating a cycle of target mRNA degradation into small 23-24 nt RNA fragments, as described for several example cases (Hamilton and Baulcombe, 1999). AtThi2 and AtThi3 activities are functionally inactivated by this RNAi approach in a tissue specific fashion. One reason we are producing doubly suppressed lines for AtThi2 and AtThi3 is that the efficiency of blocking the thiamine biosynthesis is then be the multiple of the two phenotypes. In other words, the suppressed phenotype is stronger if two genes are inactivated instead of just one. In addition, AtThi2 encodes a bifunctional enzyme, further strengthening the suppression of thiamine synthesis. If each of the three enzymes are suppressed to 10% of normal levels then the thiamine pathway is blocked to 0.1% of normal levels (i.e., $f=(0.1)^3=0.001$).

With respect to the tissue specificity of RNA interference, there is very little information as to RNAi activity being restricted to a single organ or tissue. We are not aware of examples of RNAi purposefully directed at a tissue or organ. Virus-induced RNA silencing can be naturally restricted to the veins or leaves of plants (Voinnet et al., 1999). In contrast, there is more evidence for the systemic nature of RNA-directed cosuppression from a number of sources (Citovsky and Zambryski, 2000; Fagard and Vaucheret, 2000). Grafted transgenic plants often transmitted co-suppression phenotypes to other parts of the plant. However, most of the systemic behavior reported is due to RNA virus movement and expression throughout the plant (Voinnet et al., 2000). However, these experiments are biased in nature because they were directed at exploring co-suppression and some of its systemic properties. The experiments described herein are believed to be the first using tissue-specific promoters to express interference RNAs in order to inactivate target RNAs in a tissue-specific manner. These experiments are counterintuitive because of prejudice in the art that PTGS is always systemic.

Figure 3A:
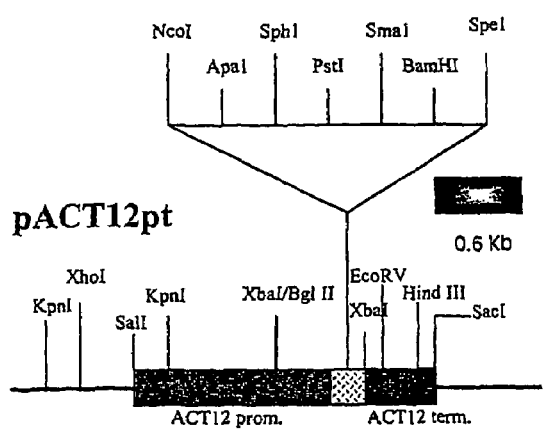
FIGS. 3A, 3B and 3C provide partial plasmid maps of pACT12pt, pACT11pt and pACT2pt, respectively.
Figure 3B:
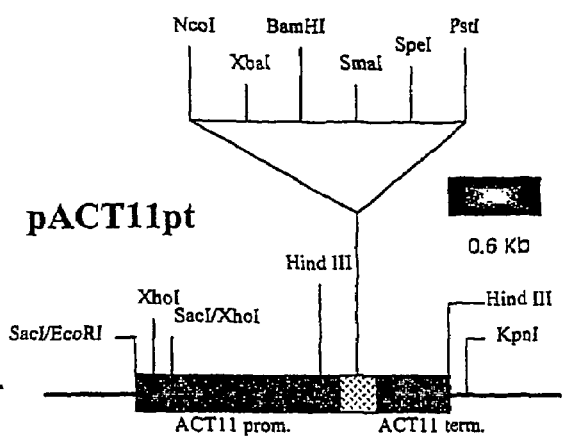
Figure 3C:
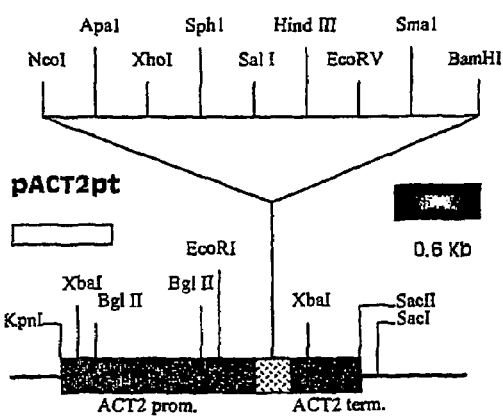

We PCR amplify cDNA sequence (AtPDC2) for one of the *Arabidopsis* AtPDC2 sequences but modify it to contain appropriate cloning sites, a mutation one codon (see FIGS. 6A-6B), with and without an epitope tag. There are five *Arabidopsis* sequences with reasonable 4044% identity overall with the well characterized bacterial *Zymomonas* sequence. We focus on the highly expressed AtPDC2 sequence (see FIGS. 6A-6B). Twenty four of the 27 resides surrounding the AtPDC2 target residue E517 are identical between the plant and bacterial sequences. We PCR amplify the *Arabidopsis* AtPDC2 cDNA from an *Arabidopsis* library using a two fragment overlap extension strategy mutating the codon for E517 to encode Q517. This cloning strategy creates the mutant cloned sequence $PDC_{E517Q}$. First, the *ArabidopsisAtPCD2* gene is modified to mutate GAG codon 517 encoding Glu to the new codon sequence CM encoding Gln. Second, the $PDC_{E517Q}$ protein product is C-terminally tagged with an HA epitope. The HA tagging allows one step purification of the protein to facilitate preparing AtPDC2-specific antibody. The resulting sequence is called $PDC_{E517Q}$. See also SEQ ID NO:7 and SEQ ID NO:8. This cDNA is cloned into the ACT11pt and ACT12pt expression vectors described above and transformed into *Arabidopsis* selecting for a linked hygromycin resistance markers. Maps of the first vectors to be used are shown in FIGS. 3A-3C. We screen plants from these two promoter systems for a dominant male-female sterility and male sterility phenotypes, respectively. Again as a simple control, the $PDC_{E517Q}$ encoding sequence is expressed from an actin ACT2pt promoter vector to make a plant whose vegetative growth is dependent upon added thiamine. The thiamine requiring phenotype depends less on the tissue/organ specificity of gene expression, so vegetative expression of the thiamine-sequestering PDC is an option for conditional plant sterility.

AtThi2, AtThi3, and AtPDC2 are soluble enzymes that are sequence homologues of bacterial sequences. Their mRNAs are translated in the cytoplasm and are specifically targeted to the prokaryotic environments (e.g., chloroplast and mitochondria). Therefore, they are efficiently expressed as native proteins in *E. coli*. A PCR amplified cDNA sequence is cloned which encodes *Arabidopsis* AtThi2 and AtThi3 without their organellar target peptides of 20 and 21 amino acids, that are removed during organellar transport in plants. A ATPDC2 cDNA is amplified from *Arabidopsis* total plant cDNA. The three sequences are given in FIGS. 4A-4C, 5A-5B and 6A-6B. Commercially available pBluescript and pET expression vectors are used. Appropriate bacterial stop codons (for LacZ), Shine-Delgarno sequences and cloning sites are added during PCR as we have explained in several previous publications in which we have described the expression of plant sequences in *E. coli* (Kandasamy et al., 1999; McKinney et al., 2001; McKinney et al., 2002). Synthetic multiple antigenic peptides (MAPs) with homology to the mature N-terminal and C-terminal 30 amino acid residues of AtThi2, AtThi3, and ATPDC2 are prepared. The MAP peptides are used as immunogens in mice to make polyclonal and monoclonal antisera to these proteins following the protocol published recently for three soluble enzymes (Li et al., 2001). Also by this established protocol the crude protein extracts from *E. coli* with and without the expressed cDNAs are used to characterize polyclonal sera and screen out monoclonal antibodies. Thus, AtThi2, AtThi3, and ATPDC2 proteins do not need to be purified for these assays. These antibodies are used in assays of AtThi2, AtThi3, and AtPDC protein levels in RNAi suppressed plants.

The thiamine B1 deficient phenotypes in RNAi-Thi2, RNAi-Thi3, and $PDC_{E473Q}$ plant lines are characterized as follows. The tissue specificity of the ACT11 promoter directs AtThi-RNAi and $PDC_{E473Q}$ gene expression to etiolated hypocotyls and reproductive tissues, which is lethal to seedling growth and mature plant reproduction, respectively. As described above the AtThi2-RNAi construct is linked to a KanR marker and the AtThi3-RNAi construct to a HygR marker. Thus, three classes of plants, KanR, HygR, and HygR+KanR, are characterized as potentially suppressed for AtThi2, AtThi3 and AtThi2+AtThi3, respectively. In order to allow RNAi suppressed plants and $PDC_{E473Q}$ plants with the strongest phenotypes to grow and reproduce, the vacuum infiltrated seed with T1 generation transformed plants are germinated on medium supplemented with thiamine (Li and Redei, 1969). Twenty RNAi plant lines for each of the three drug resistance phenotypes are grown through seed maturation on soil, while being watered with thiamine (Redei, 1969). Ten plants with the drug marker linked to $PDC_{E517Q}$ are examined. As a positive control, we also germinate KanR seed carrying the act7-2 mutation. The act7-2 mutant has no detectable phenotype, because its T-DNA insertion lies downstream from the ACT7 gene and before the next gene in *Arabidopsis*. The first inflorescence branch from each Thi suppressed and act7-2 plant is isolated in an Aracon tube and is not treated with thiamine. The remaining inflorescences are sprayed with thiamine. The unsprayed inflorescence branches are scored initially for numbers of siliques and mature seeds as compared to the number on sprayed adjacent inflorescence branches.

Thirty single transformed lines for each of the three genes (e.g., Thi2-RNAi, Thi3-RNAi, $PDC_{E517Q}$) and thirty doubly transformed lines blocked for thiamine biosynthesis (i.e., Thi2-RNAi and Thi3-RNAi) are characterized further at the molecular level. Plant extracts from young siliques taken from the T2 generation are assayed for AtThi2, AtThi3, and $PDC_{E517Q}$ protein levels are determined on Western blots using the above described antibodies or the commercial HA antibody. Like the strong expression of the ACT11 promoter in siliques, these tissues also show a significant reduction in Thi protein expression or increase in $PDC_{E517Q}$ protein expression. The actual stage in plant growth and tissue that first shows a phenotype is noted. Without wishing to be bound by theory, it is believed that the transgenic plant forms sepals, petals, carpels, and anthers, but fails to form embryos or mature pollen. The plant may begin to form embryos, but those embryos die during development.

RNAi was expressed to knock down HTK or TPP/PPK in vegetative organs and tissues produced almost no phenotype; these plants were essentially the same as control plants. By contrast, RNA interference expressed to decrease HTK or TPP/PPK in reproductive organs and tissues produced strong sterility phenotypes. An A2pt:Thi3Ri-1 HTK resulted in a phenotype in which the plants were fertile and 80-100% of normal size. These plants exhibited a slight reduction in initial growth rates but only moderate long-term dwarfing. The adult plants appeared almost normal. The A2 (Actin 2) promoter directs expression in vegetative tissues. Examination of plant tissues genetically modified with an A2pt:GUS construct indicated that expression occurred in seedlings, leaves, roots, petal and sepals.

An A11pt:Thi3-RiRi-1 HTK construct resulted in plants that were partially or fully sterile. The A11 (actin 11) promoter directs expression in female and male organs and tissues of the plant. This was confirmed using an A11:GUS fusion construct. Expression of GUS was observed in ovule, embryo, endosperm, and mature pollen. Female-male specificity was observed. All the A11pt:Thi3Ri-1 plants are partially or fully sterile. About 20% of the $T_1$ lines make few or no siliques. The RNAi targeted only about 70 nucleotides of the much larger Thi3 transcript. From those partially sterile liens that produce a few siliques, most of the seeds that are produced are sterile (aborted or dead). An A11pt:Thi3Ri-1 TPP/PPK construct resulted in plants that were partially or completely sterile despite the elaboration of large numbers of flowers. Whereas wild-type seeds rarely include nonviable seeds, 20 to 100% of the seeds produced from this construct are inviable (seeds are dark brown and shriveled).

An A12pt:Thi2Ri-1 TPP/PPK construct resulted in a fully male sterile phenotype. The A12 (actin 12) promoter directs expression in late in pollen development. Expression was examined using an A12pt:GUS fusion construct; activity was observed in the inflorescence of the genetically modified *Arabidopsis*.

Three lines already characterized as fully sterile in a parent plant and known to be suppressed for the Thi target genes are selected for a more quantitative examine examination of sterility in a population. One hundred T3 generation RNAi or $PDC_{E517Q}$ expressing seedlings germinated with thiamine are grown to maturity on soil lacking added thiamine. When the average height of the first two inflorescences stems in the population reaches about 12 in., each plant is scored for numbers of developing siliques and seeds. This process takes about four to five weeks. Then half the plants are sprayed with thiamine and the sprayed, and unsprayed plants are scored again two weeks later for siliques and seeds. Wild-type plants are scored at the same two times as positive controls.

Based on homology to *E. coli*, yeast, and *S. pombe* sequences, we have identified two *Arabidopsis* targets, AtThi2 and AtThi3, to suppress thiamine biosynthesis and one protein product $PDC_{E473Q}$ to sequester thiamine. Together the two Thi genes determine three essential enzymatic steps in thiamine synthesis. AtThi2 and AtThi3 are both undoubtedly essential to thiamine biosynthesis. The genes are inactivated individually and together by an RNAi strategy using a reproductive tissue-specific actin promoter system. Each is shown to be an essential gene for the development of siliques and seeds. *Arabidopsis* AtPDC2 genes were identified by homology to bacterial and yeast pyruvate decarboxylase sequences and form a small gene family in *Arabidopsis*. In bacteria and yeast, the mutant form of the enzyme $PDC_{E473Q}$ has lost 99% of its enzyme activity but has greatly enhanced binding capacity for thiamine. This strong binding should sequester any thiamine present in these cells, including any that is transported in from adjacent tissues. Thiamine-deficient plants are shown to have a male-female sterile or male-sterile TDCS phenotypes depending upon the promoter used. The TDCS phenotypes are rescued by direct application of thiamine to the plants or their soil. In the future, this system is applied to TDCS trees, shrubs, and grasses to enhance there use in phytoremediation of toxic elements and organics such as our previously described mercury and arsenic resistant plants (Meagher, 2000; Meagher et al., 2000; Bizily et al., 2002; Dhankher et al., 2002). This flexible system of TDCS is also easily applied to forestry for more efficient wood or fiber production and to the hybrid seed industry.

Targeted gene suppression in plants can be achieved through the induction of RNA interference (RNAi), also known as post-transcriptional gene silencing. This is accomplished through in vivo production of an RNA species containing a double stranded region composed of sequence homologous to a segment of the mRNA to be targeted. Production of this dsRNA leads to the induction of RNAi and subsequence degradation of the corresponding mRNA.

Figure 7:
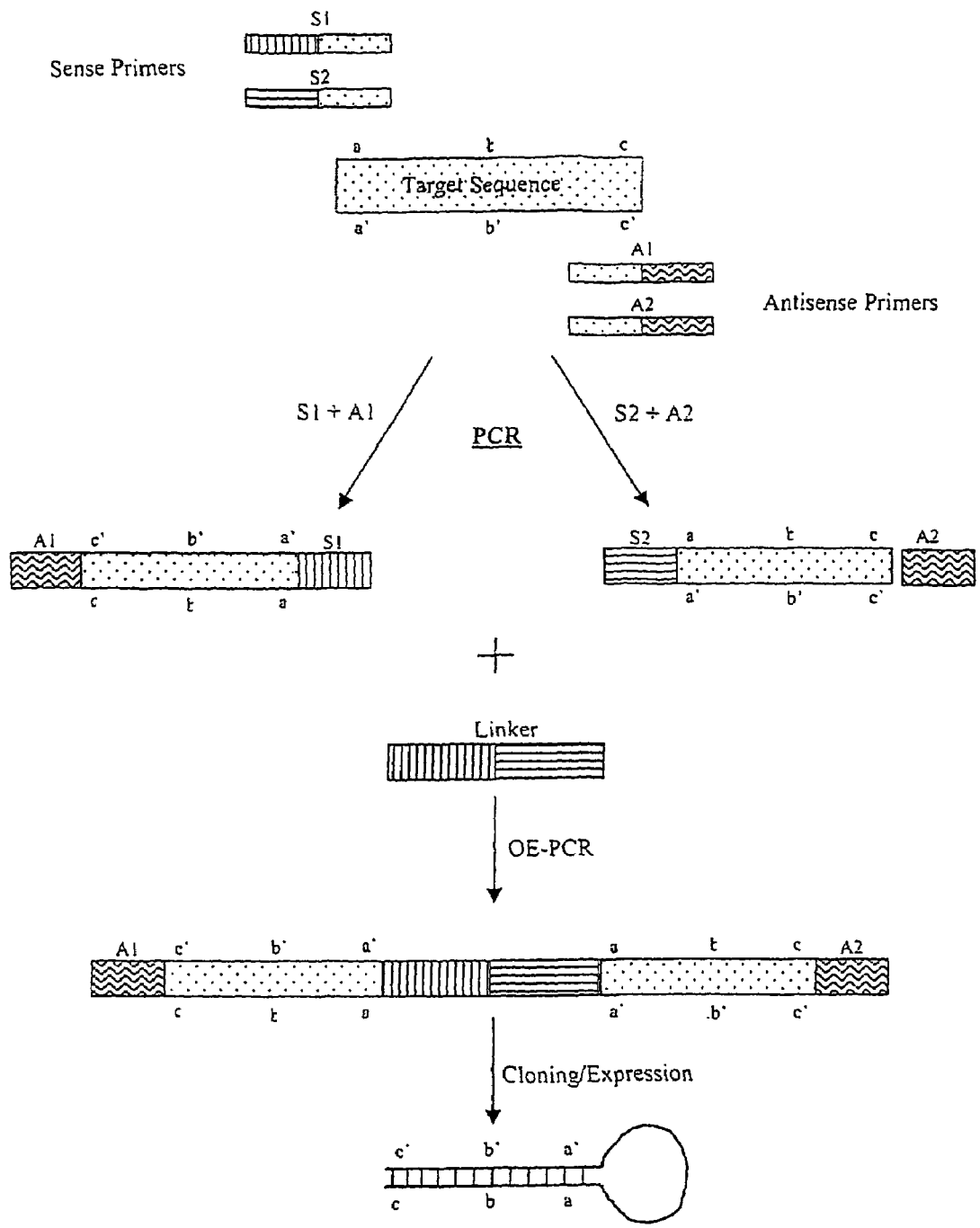
FIG. 7 diagrammatically illustrates the steps for the rapid cloning of RNAi constructs using overlap extension polymerase chain reaction (OE-PCR), as described herein below.

The Overlap Extension-PCR (OE-PCR) procedure can be used to generate a DNA molecule containing two copies of the target sequence in inverted orientation of one another, as shown in FIG. 7. The transcript produced from this cloned DNA molecule forms the requisite double-stranded structure needed to trigger RNAi; thus, transformation of plants with such a construct leads to a loss of function phenotype for the targeted gene [Chuang and Meyerowitz, (2000) *Proc. Natl. Acad. Sci. USA* 97:4985-4990].

The OE-PCR procedure requires three DNA fragments: the linker fragment, a target sequence fragment with homology to the 5' end of the linker, and a second target sequence fragment which is identical to the first except that it has homology to the 3' end of the linker. Each of these fragments is produced in a separate PCR, and all three are then combined in an OE-PCR to generate the final product (see FIG. 7), which is treated with appropriate restriction enzymes and cloned into an expression vector.

The linker fragment consists of a 1 kb internal segment of the GUS gene, which is amplified with the following primers:

```
GUS Sense:
5'-CCG ACG AAA ACG GCA AGA AAA AGC    (SEQ ID NO:9)
AGT-3'

GUS Antisense:
5'-CCA GAA GTT CTT TTT CCA GTA CCT-   (SEQ ID NO:10)
3'
```

The target sequence is desirably 100 bp or more in length and consists of sequence unique to the gene to be suppressed. The sequence is amplified in two separate reactions, using different primer sets for each reaction, as shown in FIG. 7. Thus, four primers are required: two sense strand primers and two antisense strand primers. Two fragments having identical internal sequence (the target sequence) are produced, but they differ at their ends such that each fragment overlaps a different end of the linker and contains unique restriction sites for use in cloning.

The two sense strand primers S1 and S2 contain at their 3' ends approximately 25 nt of homology to the upstream end of the target sequence, and this region is identical in both primers. Immediately 5' to this region is 20 nt of homology to one end of the GUS linker. In this region the S1 oligonucleotide is identical to the antisense strand of the upstream end of the linker, and the S2 oligonucleotide is identical to the sense strand of the downstream end of the linker.

```
S1:
5'TTT CTT GCC GTT TTC GTC GG + 25nt  (SEQ ID NO:11)
target "A"-3'
GUS homology S2:
5'-ACT GGA AAA AGA ACT TCT GG + 25nt (SEQ ID NO:12)
target "A"-3'
```

The antisense strand primers A1 and A2 both have at their 3' ends an identical 25 nt region of homology to the downstream end of the target sequence. Immediately 5' to this segment are unique restriction sites (different ones in each primer) that can be used in directional cloning of the final product. Each oligo then has at its 5' end a unique "clamp" sequence of 21 nt. These unique sequences serve as priming sites for "clamp" primers used to amplify the full length OE-PCT product at the end of the procedure. The "clamp" primers are identical to the "clamps" in each oligo shown below. The primer Clamp-sense is the underlined sequence in A1 below, and Clamp-antisense is the underlined sequence in A2. Amplification of the final product using the clamp primers helps to reduce the background generated in OE-PCT, as explained below.

```
A1: 5'-TGA TAG TGA TAG TGA TAG TGA (SEQ ID NO:13) +
    restriction sites + 25nt target "C'"-3'
Clamp 1 (underlined)

A2: 5'-AGC GTT AGC GTT AGC GTT AGC (SEQ ID NO:14) +
    restriction sites + 25nt target "C'"-3'
Clamp 2 (underlined)
```

The GUS linker fragment is amplified from pBI121 using the primers GUS-sense and GUS-antisense. The 50 µL reaction contains 200 ng of pBI121, 1.5 mM $MgCl_2$, 0.2 mM each dNTP, 4 pmol of each primer, and 2 units of Taq DNA polymerase in 1×PCR buffer. The reaction is run through 1 cycle of 94° for 3 min and 45 cycles of 94° for 45 sec, 55° for 50 sec, 72° for 1 min, followed by a final extension at 72° for 5 min. The reaction product is purified with the Qiagen PCR purification kit (Valencia, Calif.) and eluted in 50 µL of water.

We have observed that gel purification of any of the three fragments tends to foul the OE-PCR. Therefore in lieu of gel purification, small amounts of primer and a large number of cycles are used to reduced carry-over of GUS primers. Carry-over of large amounts of these primers into the OE-PCR promotes formation of an additional smaller product which results from amplification of the OE product of the GUS linker and one or the other target fragment.

The target sequence fragments are amplified from a plasmid cDNA library in two separate reactions; one using primers S1 and A1, and another using primers S2 and A2 (see FIG. 7). Conditions are identical for both reactions and are as follows: 1 µg cDNA library, 1.5 mM $MgCl_2$, 0.2 mM each dNTP, 16.25 pmol of each primer, and 2 units of Taq DNA polymerase in a 50 µL total volume of 1×PCR buffer. The reactions are run through 1 cycle of 94° for 3 min and 30 cycles of 94° for 50 sec, 55° for 50 sec, 72° for 50 sec, followed by a final extension at 72° for 3 min. The products are purified using the Qiagen PCR purification kit and eluted in 50 µL of water.

The three purified PCR products are combined in a 1:1:1 ratio (approximately 20 ng of each) in the following OE-PCR reaction: 1.5 mM $MgCl_2$, 0.2 mM each dNTP, and 2 units of Taq DNA polymerase in 50 µL total volume of 1×PCR buffer. Thermal cycling consists of one cycle of 94° for 2 min and 8 cycles of 94° for 50 sec, 55° for 50 sec, 72° for 1 min, followed by a final extension at 72° for 5 min. See FIG. 7.

The final full length OE product is amplified with primers Clamp-sense and Clamp-antisense using 1 µL of the OE-PCR as template under the following conditions: 1.5 mM $MgCl_2$, 0.2 mM each dNTP, 16.25 pmol of each primer, and 2 units of Taq DNA polymerase in 50 µL total volume of 1×PCR buffer. The reaction is run through 1 cycle of 94° for 2 min and 20 cycles of 94° for 1 min, 56° for 1 min, 720 for 1 min 30 sec, followed by a final extension at 72° for 5 min. The full-length product is then gel purified and cloned into an appropriate vector where it can be transcribed into the stem-loop RNA shown in FIG. 7.

Techniques and agents for introducing and selecting for the presence of heterologous DNA in plant cells and/or tissue are well-known. Genetic markers allowing for the selection of heterologous DNA in plant cells are well-known, e.g., genes carrying resistance to an antibiotic such as kanamycin, hygromycin, gentamycin, or bleomycin. The marker allows for selection of successfully transformed plant cells growing in the medium containing the appropriate antibiotic because they will carry the corresponding resistance gene. In most cases the heterologous DNA which is inserted into plant cells contains a gene which encodes a selectable marker such as an antibiotic resistance marker, but this is not mandatory. An exemplary drug resistance marker is the gene whose expression results in kanamycin resistance, i.e., the chimeric gene containing nopaline synthetase promoter, Tn5 neomycin phosphotransferase II and nopaline synthetase 3' non-translated region described by Rogers et al., *Methods for Plant Molecular Biology*, A. Weissbach and H. Weissbach, eds., Academic Press, Inc., San Diego, Calif. (1988).

Techniques for genetically engineering plant cells and/or tissue with an expression cassette comprising an inducible promoter or chimeric promoter fused to a heterologous coding sequence and a transcription termination sequence are to be introduced into the plant cell or tissue by *Agrobacterium*-mediated transformation, electroporation, microinjection, particle bombardment or other techniques known to the art. The expression cassette advantageously further contains a marker allowing selection of the heterologous DNA in the plant cell, e.g., a gene carrying resistance to an antibiotic such as kanamycin, hygromycin, gentamicin, or bleomycin.

The choice of vector in which the DNA of interest is operatively linked depends directly, as is well known in the art, on the functional properties desired, e.g., replication, protein expression, and the host cell to be transformed, these being limitations inherent in the art of constructing recombinant DNA molecules. The vector desirably includes a prokaryotic replicon, i.e., a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline, among other selective agents. The neomycin phosphotransferase gene has the advantage that it is expressed in eukaryotic as well as prokaryotic cells.

Those vectors that include a prokaryotic replicon also typically include convenient restriction sites for insertion of a recombinant DNA molecule of the present invention. Typical of such vector plasmids are pUC8, pUC9, pBR322, and pBR329 available from BioRad Laboratories (Richmond, Calif.) and pPL, pK and K223 available from Pharmacia (Piscataway, N.J.), and pBLUESCRIPT and pBS available from Stratagene (La Jolla, Calif.). A vector of the present invention may also be a Lambda phage vector including those Lambda vectors described in *Molecular Cloning: A Laboratory Manual, Second Edition*, Maniatis et al., eds., Cold Spring Harbor Press (1989) and the Lambda ZAP vectors available from Stratagene (La Jolla, Calif.). Other exemplary vectors include pCMU [Nilsson et al. (1989) Cell 58:707]. Other appropriate vectors may also be synthesized, according to known methods; for example, vectors pCMU/K$^b$ and pCMUII used in various applications herein are modifications of pCMUIV (Nilson et al., supra).

Typical expression vectors capable of expressing a recombinant nucleic acid sequence in plant cells and capable of directing stable integration within the host plant cell include vectors derived from the tumor-inducing (Ti) plasmid of *Agrobacterium tumefaciens* described by Rogers et al. (1987) *Meth. in Enzymol.* 153:253-277, and several other expression vector systems known to function in plants. See for example, Verma et al., No. WO87/00551; Cocking and Davey (1987) *Science* 236:1259-1262.

A transgenic plant can be produced by any means known to the art, including but not limited to *Agrobacterium tumefaciens*-mediated DNA transfer, *Agrobacterium rhizogenes*-mediated DNA transfer, both preferably with a disarmed T-DNA vector, electroporation, direct DNA transfer, liposomes, diffusion, microinjection, virus vectors, calcium phosphate, and particle bombardment (See Davey et al. (1989) *Plant Mol. Biol.* 13:275; Walden and Schell (1990) *Eur. J. Biochem.* 192:563; Joersbo and Burnstedt (1991) *Physiol Plant.* 81:256; Potrykus (1991) *Annu. Rev. Plant Physiol. Plant Mol. Biol.* 42:205; Gasser and Fraley (1989) *Science* 244:1293; Leemans (1993) *Bio/Technology* 11:522; Beck et al. (1993) *Bio/Technology* 11:1524; Koziel et al. (1993) *Bio/Technology* 11:194; and Vasil et al. (1993) Bio/Technology. 11:1533.). Techniques are well-known to the art for the introduction of DNA into monocots as well as dicots, as are the techniques for culturing such plant tissues and regenerating those tissues.

Many of the procedures useful for practicing the present invention, whether or not described herein in detail, are well known to those skilled in the art of plant molecular biology. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1-4, Plenum Press, New York, Kaufman (1987) in *Genetic Engineering Principles and Methods*, J. K. Setlow, ed., Plenum Press, NY, pp. 155-198; Fitchen et al. (1993) *Annu. Rev. Microbiol.* 47:739-764; Tolstoshev et al. (1993) in *Genomic Research in Molecular Medicine and Virology*, Academic Press. Abbreviations and nomenclature, where employed, are deemed standard in the field and commonly used in professional journals as cited herein.

All references and patent documents cited herein are incorporated in their entireties to the extent that there is no inconsistency with the present disclosure.

Where features or aspects of the invention are described in terms of Markush groups or other groupings of alternatives, those skilled in the art will recognize that the invention is also thereby described in terms of any individual member or subgroup of members of the Markush group or other group.

The examples provided herein are for illustrative purposes, and are not intended to limit the scope of the invention as claimed herein. Any variations in the exemplified articles which occur to the skilled artisan are intended to fall within the scope of the present invention.

REFERENCES CITED IN THE TEXT OF THE APPLICATION

Albertsen, M., and Howard, J. (1999). Induction of male sterility in plants by expression of high levels of avidin, WO 99/04023.

*Arabidopsis* Genome Initiative. (2000). Analysis of the genome sequence of the flowering plant *Arabidopsis thaliana*. Nature 408:796-815.

Bariola, P. A., Macintosh, G. C., and Green, P. J. (1999). Regulation of S-like ribonuclease levels in *Arabidopsis*. Antisense inhibition of RNS1 or RNS2 elevates anthocyanin accumulation. *Plant Physiol.* 119:331-342.

Bevan, M. W. (1984). Binary *Agrobacterium* vectors for plant transformation. *Nucl. Acids Res.* 12:8711-8721.

Bizily, S., Kim, R., Kandasamy, M., and Meagher, R. B. (2003). Subcellular targeting of methylmercury lyase enhances its specific activity for organic mercury detoxification in plants. *Plant Physiol.* 131:463-471.

Bouvier, F., d'Harlingue, A., Suire, C., Backhaus, R. A., and Camara, B. (1998). Dedicated roles of plastid transketolases during the early onset of isoprenoid biogenesis in pepper fruits1. *Plant Physiol.* 117:1423-1431.

Brown, G., and Williamson, J. (1987). 34. Biosynthesis of folic acid, riboflavin, thiamine, and pantothenic acid. In: *Escherichia coli* and *Salmonella typhimurium*, 1, F. Neidhardt, eds (Washington, D.C.: American Society for Microbiology), pp. 521-538.

Chabregas, S. M., Luche, D. D., Farias, L. P., Ribeiro, A. F., van Sluys, M. A., Menck, C. F., and Silva-Filho, M. C. (2001). Dual targeting properties of the N-terminal signal sequence of *Arabidopsis thaliana* THI 1 protein to mitochondria and chloroplasts. *Plant Mol. Biol.* 46:639-650.

Chang, A. K., and Duggleby, R. G. (1997). Expression, purification and characterization of *Arabidopsis thaliana* acetohydroxyacid synthase. *Biochem. J.* 327:161-169.

Chang, A. K., Nixon, P. F., and Duggleby, R. G. (1999). Aspartate-27 and glutamate-473 are involved in catalysis by *Zymomonas mobilis* pyruvate decarboxylase. *Biochem. J.* 339:255-260.

Chuang, C. F., and Meyerowitz, E. M. (2000). Specific and heritable genetic interference by double-stranded RNA in *Arabidopsis thaliana*. *Proc Natl Acad Sci USA* 97:4985-4990.

Citovsky, V., and Zambryski, P. (2000). Systemic transport of RNA in plants. *Trends Plant Sci.* 5:52-54.

Dhankher, O. P., Li, Y., Rosen, B. P., Shi, J., Salt, D., Senecoff, J. F., Sashti, N. A., and Meagher, R. B. (2002). Engineering tolerance and hyperaccumulation of arsenic in plants by combining arsenate reductase and gamma-glutamylcysteine synthetase expression. *Nat. Biotechnol.* 20:1140-1145.

Fagard, M., and Vaucheret, H. (2000). Systemic silencing signal(s). *Plant Mol. Biol.* 43:285-293.

Goffeau, A., Barrell, B. G., Bussey, H., Davis, R. W., Dujon, B., Feldmann, H., Galibert, F., Hoheisel, J. D., Jacq, C., Johnston, M., Louis, E. J., Mewes, H. W., Murakami, Y., Philippsen, P., Tettelin, H., and Oliver, S. G. (1996). Life with 6000 genes. *Science* 274:546, 563-567.

Hamilton, A. J., and Baulcombe, D. C. (1999). A species of small antisense RNA in posttranscriptional gene silencing in plants [see comments]. *Science* 286:950-2.

Huang, S., An, Y.-Q., McDowell, J. M., McKinney, E. C., and Meagher, R. B. (1996). The *Arabidopsis* ACT4/ACT12 actin gene subclass is strongly expressed in post-mitotic pollen. *Plant J.* 10:189-202.

Huang, S., An, Y.-Q., McDowell, J. M., McKinney, E. C., and Meagher, R. B. (1997). The *Arabidopsis* ACT11 actin gene is strongly expressed in tissues of the emerging inflorescence, pollen and developing ovules. *Plant Mol. Biol.* 33:125-139.

Kandasamy, M. K., McKinney, E., and Meagher, R. B. (1999). The late pollen-specific actins in angiosperms. *Plant J.* 18:681-691.

Konig, S., Svergun, D. I., Volkov, V. V., Feigin, L. A., and Koch, M. H. (1998). Small-angle X-ray solution-scattering studies on ligand-induced subunit interactions of the thiamine diphosphate dependent enzyme pyruvate decarboxylase from different organisms. *Biochemistry* 37:5329-5334.

Ledoux, L., Huart, R., and Jacobs, M. (1974). DNA-mediated genetic correction of thiamineless *Arabidopsis thaliana*. *Nature* 249:17-21.

Li, S. L., and Redel, G. P. (1969). Thiamine mutants of the crucifer, *Arabidopsis*. *Biochem. Genet.* 3:163-170.

Li, Y., Kandasamy, M. K., and Meagher, R. B. (2001). Rapid isolation of monoclonal antibodies: monitoring enzymes in the phytochelatin synthesis pathway. *Plant Physiol.* 127:711-719.

Lu, G., Dobritzsch, D., Baumann, S., Schneider, G., and Konig, S. (2000). The structural basis of substrate activation in yeast pyruvate decarboxylase. A crystallographic and kinetic study. *Eur J. Biochem.* 267:861-868.

Machado, C. R., de Oliveira, R. L., Boiteux, S., Praekelt, U. M., Meacock, P. A., and Menck, C. F. (1996). Thi1, a thiamine biosynthetic gene in *Arabidopsis thaliana*, complements bacterial defects in DNA repair. *Plant Mol. Biol.* 31:585-593.

Machado, C. R., Praekelt, U. M., de Oliveira, R. C., Barbosa, A. C., Byrne, K. L., Meacock, P. A., and Menck, C. F. (1997). Dual role for the yeast THI4 gene in thiamine biosynthesis and DNA damage tolerance. *J. Mol. Biol.* 273:114-121.

Manetti, A. G., Rosetto, M., and Maundrell, K. G. (1994). nmt2 of fission yeast: a second thiamine-repressible gene co-ordinately regulated with nmt1. *Yeast* 10:1075-1082.

McKinney, E. C., Kandasamy, M. K., and Meagher, R. B. (2001). Small changes in the regulation of one *Arabidopsis* profilin isovariant, prf1, alter seedling development. *Plant Cell* 13:1179-1191.

McKinney, E. C., Kandasamy, M. K., and Meagher, R. B. (2002). *Arabidopsis* contains ancient classes of differentially expressed actin-related protein genes. Plant Physiol 128: 997-1007.

Meagher, R. B. (2000). Phytoremediation of toxic elemental and organic pollutants. Curr. Opin. Plant Biol. 3: 153-162.

Meagher, R. B., Rugh, C. L., Kandasamy, M. K., Gragson, G., and Wang, N. J. (2000). Engineered phytoremediation of mercury pollution in soil and water using bacterial genes. In: Phytoremediation of Contaminated Soil and Water, N. Terry, and G. Banuelos, eds (Boca Raton: Lewis Publishers), pp. 203-221.

Nishimura, H., Kawasaki, Y., Kaneko, Y., Nosaka, K., and Iwashima, A. (1992). A positive regulatory gene, THI3, is required for thiamine metabolism in *Saccharomyces cerevisiae*. *J. Bacteriol.* 174:4701-4706.

Nishimura, H., Kawasaki, Y., Nosaka, K., Kaneko, Y., and Iwashima, A. (1991). A constitutive thiamine metabolism mutation, thi80, causing reduced thiamine pyrophosphokinase activity in *Saccharomyces cerevisiae*. *J. Bacteriol.* 173:2716-2719.

Nosaka, K., Kaneko, Y., Nishimura, H., and Iwashima, A. (1993). Isolation and characterization of a thiamin pyrophosphokinase gene, THI80, from *Saccharomyces cerevisiae*. *J. Biol. Chem.* 268:17440-17447.

Perez-Prat, E., and van Lookeren Campagne, M. M. (2002). Hybrid seed production and the challenge of propagating male-sterile plants. *Trends Plant Sci.* 7:199-203.

Preuss, D., Rhee, S. Y., and Davis, R. W. (1994). Tetrad analysis made possible in *Arabidopsis* by a mutation of the QUARTET (QRT) genes, *Science* 264:1458-1460.

Rapala-Kozik, M., Chernikevich, I. P., and Kozik, A. (1999). Ligand-protein interaction in plant seed thiamine-binding proteins. Binding of various thiamine analogues to the sepharose-immobilized buckwheat-seed protein. *J. Protein Chem.* 18:721-728.

Redei, G., and Li, S. (1969). Effects of x rays and ethyl methanesulfonate on the chlorophyll B locus in the soma and on the thiamine loci in the germine of *Arabidopsis*. *Genetics* 61:453-459.

Voinnet, O., Lederer, C., and Baulcombe, D. C. (2000). A viral movement protein prevents spread of the gene silencing signal in *Nicotiana benthamiana*. *Cell* 103:157-167.

Voinnet, O., Pinto, Y. M., and Baulcombe, D. C. (1999). Suppression of gene silencing: a general strategy used by diverse DNA and RNA viruses of plants. *Proc. Natl. Acad. Sci. USA* 96:14147-14152.

Watanabe, K., Chikushi, K., Adachi, T., Shimizu, M., Yoshida, T., and Mitsunaga, T. (1998). Thiamin-binding protein from sunflower seeds. *J. Nutr. Sci. Vitaminol.* (Tokyo) 44:665-672.

What is claimed is:

1. A nucleic acid molecule comprising an expressed portion and a plant-expressible transcription regulatory sequence which specifically directs expression of an expressed portion in male or male and female reproductive tissue, wherein said transcription regulatory sequence is an *Arabidopsis thaliana* Act11 or Act12 transcription regulatory sequence, wherein said transcription regulatory sequence is operably linked to said expressed portion and wherein said expressed portion expresses an antisense RNA or an interference RNA specific for a plant thiamine biosynthetic gene, wherein said expressed portion expresses an antisense RNA or an interference RNA each specific for an AtThi2 or an AtThi3 sequence, said expressed portion being sufficient to cause conditional sterility when expressed specifically in the reproductive tissue of a transgenic plant.

2. A method of using the nucleic acid molecule of claim 1 to produce a plant which is sterile in the absence of exogenous thiamine, said method comprising the steps of introducing the nucleic acid molecule into a plant cell or into plant tissue, selecting for the presence of the nucleic acid molecule to produce a transgenic plant cell or transgenic plant tissue, and regenerating a plant from the transgenic plant cell or transgenic plant tissue, whereby a plant with a conditionally sterile phenotype is produced.

3. The method of claim 2, wherein the transgenic plant is a conditionally male sterile plant.

4. The method of claim 2, wherein the transgenic plant is a conditionally male and female sterile plant.

5. The method of claim 2, wherein said transgenic plant is a dicotyledonous plant.

6. The method of claim 5, wherein said transgenic plant is a member of the Solanaceae.

7. The method of claim 5, wherein said transgenic plant is *Arabidopsis*.

8. The method of claim 5, wherein the plant is a poplar or a cottonwood.

9. The method of claim 2, wherein said transgenic plant is a monocotyledonous plant.

10. The method of claim 2, wherein said transgenic plant is a gymnosperm.

11. The method of claim 10, wherein said transgenic plant is a member of the Coniferae.

12. A transgenic plant produced by the method of claim 2.

* * * * *